United States Patent [19]

Bauer, Jr. et al.

[11] Patent Number: 5,990,343
[45] Date of Patent: *Nov. 23, 1999

[54] PROCESS FOR PRODUCING BUTYL ACRYLATE

[75] Inventors: William Bauer, Jr., Huntingdon Valley; Josefina Tseng Chapman, Norristown; Mario Giuseppe Luciano Mirabelli, Horsham, all of Pa.; Jeremia Jesaja Venter, Seabrook, Tex.

[73] Assignee: Rohm and Haas Company, Phila., Pa.

[*] Notice: This patent is subject to a terminal disclaimer.

[21] Appl. No.: 09/049,483

[22] Filed: Mar. 27, 1998

Related U.S. Application Data

[63] Continuation of application No. 08/797,380, Feb. 7, 1997, Pat. No. 5,877,345.

[51] Int. Cl.$^6$ ............ C07C 67/48; C07C 51/42; C07C 27/26
[52] U.S. Cl. ............ 560/218; 562/600; 568/913
[58] Field of Search ............ 560/218; 562/600; 568/913

[56] References Cited

U.S. PATENT DOCUMENTS

| | | |
|---|---|---|
| 3,539,621 | 11/1970 | Cipollone et al. |
| 3,686,268 | 8/1972 | Jobert et al. |
| 3,846,488 | 11/1974 | Otsuki et al. |
| 3,855,081 | 12/1974 | Brown. |
| 3,868,410 | 2/1975 | Horlenko et al. |
| 3,894,076 | 7/1975 | Van Duyne et al. |
| 4,012,439 | 3/1977 | Erpenbach. |
| 4,175,089 | 11/1979 | Heiba et al. |
| 4,280,010 | 7/1981 | Erpenbach et al. |
| 4,435,539 | 3/1984 | Witiak. |
| 4,464,229 | 8/1984 | Sato et al. |
| 4,507,495 | 3/1985 | Dougherty et al. |
| 4,618,709 | 10/1986 | Sada et al. |
| 4,671,857 | 6/1987 | Johnson. |
| 4,748,268 | 5/1988 | Pietsch et al. |
| 4,814,493 | 3/1989 | Dougherty et al. |
| 4,833,267 | 5/1989 | Nakashima et al. |
| 4,889,950 | 12/1989 | Bott et al. |
| 4,925,981 | 5/1990 | Shimizu et al. |
| 4,968,834 | 11/1990 | Smith et al. |
| 5,028,735 | 7/1991 | Segawa et al. |
| 5,087,744 | 2/1992 | Krabetz. |
| 5,151,547 | 9/1992 | Sato et al. |
| 5,248,819 | 9/1993 | Matsumoto et al. |
| 5,315,037 | 5/1994 | Sakamoto. |
| 5,482,597 | 6/1996 | Herbst et al. |
| 5,571,386 | 11/1996 | Bauer et al. |
| 5,606,102 | 2/1997 | Fauconet et al. ............ 560/205 |

FOREIGN PATENT DOCUMENTS

| | | |
|---|---|---|
| 270999 | 6/1988 | European Pat. Off. |
| 271371 | 6/1988 | European Pat. Off. |
| 609127 | 1/1994 | European Pat. Off. |
| 3441207 | 5/1985 | Germany. |
| 8128337 | 7/1983 | Japan. |
| 9093027 | 5/1984 | Japan. |
| 2145044 | 6/1987 | Japan. |
| 100168 | 4/1989 | Japan. |

*Primary Examiner*—Paul J. Killos
*Assistant Examiner*—J. Parsa
*Attorney, Agent, or Firm*—John Lemanowicz; Kevin Gironda

[57] ABSTRACT

An improved process for producing n-butyl acrylate in high yield and high purity substantially free of acrylic acid, incorporates one or more of the following new process components in an acid-catalyzed esterification process for producing n-butyl acrylate:

1. A hydrolytic recovery component, wherein heavy end adducts produced during the acid-catalyzed esterification are hydrolyzed, recovered, and recycled as valuable reactants from a hydrolytic recovery unit (HRU);

2. A cracking reactor component, preferably used with the HRU, wherein additional valuable reactants are recovered and recycled after treatment in the cracking reactor; and 3. A new distillative component, wherein a crude n-butyl acrylate stream is efficiently distilled in an aqueous mode through an acrylic acid separation column, thereby providing n-butyl acrylate substantially free of acrylic acid and in high yield.

The first two components also are applicable to acid-catalyzed processes producing $C_1$ to $C_4$ alkyl acrylates. A continuous process producing n-butyl acrylate incorporating all new process components also is disclosed.

6 Claims, 2 Drawing Sheets

PROCESS FOR PRODUCING BUTYL ACRYLATE

This application is a continuation of U.S. patent application Ser. No. 08/797,380 filed Feb. 7, 1997, now U.S. Pat. No. 5,877,345.

The present invention relates to an improved process for producing butyl acrylate. More specifically, the invention relates to a new method of distilling, and of recovering and recycling normal butanol ("BuOH"), acrylic acid ("AA"), and normal butyl acrylate ("BA") from one or more process streams in an acid-catalyzed esterif-ication process for BA. The invention encompasses two new process components, one related to the hydrolytic recovery of valuable reactants from their higher boiling adducts, and a second component related to improved distillation of a crude product yielding BA substantially free of AA. The hydrolytic recovery component of the invention also is useful in processes for producing selected acrylic esters, in addition to BA. Most specifically, the invention relates to a highly efficient, continuous process for producing BA in high purity and high yield.

Direct esterification of AA with an alcohol is an equilibrium process. The equilibrium constant determines the net rate and extent of conversion of AA and alcohol; for continued high rates of conversion the mixture must not approach equilibrium. Conventionally, an excess of alcohol over AA is employed and water of esterification is removed distillatively as its azeotrope with alcohol and ester to maintain a high rate of conversion of AA. The azeotrope is removed via a distillation column mounted directly on an esterification reactor. In the case of methyl or ethyl esters, the water of esterification, excess alcohol, and product ester are removed from the head of the distillation column and are substantially free of AA. Water extraction removes the alcohol which is concentrated distillatively for recycle to the reactor. The washed ester is azeotropically dehydrated and finally distilled to provide the pure ester product. In butyl acrylate production, however, the separation of acrylic acid from water of reaction, excess alcohol, and product ester is more difficult, and the distillate from the esterification reactor in a continuous process typically contains 1–3% AA. This AA typically is extracted into aqueous caustic. Although it is possible to recover some of this AA from the resulting aqueous salt solution by acidification with a strong acid followed by extraction into an organic solvent, e.g. butyl acrylate or butyl acrylate/butanol mixture, significant loss to a large aqueous waste stream is unavoidable. The butyl acrylate and excess butanol are next azeotropically dehydrated wherein excess butanol is separated from the product ester as a butanol/butyl acrylate azeotrope for recycle to the esterification reaction. A final distillation provides pure butyl acrylate. In all cases a small bleed stream is removed from the esterification reactor and a small bottoms stream is taken from the final product distillation to remove high boiling byproducts and inhibitor residues from the process. These streams are stripped to recover free AA, alcohol, and alkyl acrylate values, but little or none of the values present within the high boiling byproducts are recovered. Thus, the conventional processes for producing $C_1$–$C_4$ esters suffer from yield losses to high boiling byproducts, and the $C_4$ process further suffers from direct losses of AA because of the difficulty in separating AA from butanol, water, and ester.

In the art of recovering and recycling reactants from their higher boiling adducts formed during processing (so called "heavy ends;" in BA production these include, for example, butyl β-butoxypropionate and esters of sulfuric acid), there has been only limited success. For example, in ethyl acrylate ("EA") production from ethylene and AA, U.S. Pat. No. 4,968,834 ('834) describes a process for recovering EA from a "spent black acid" stream containing sulfuric acid residues and other adducts bled from the bottom of a distillation column. The '834 process uses an alcoholic solvent to facilitate an overhead distillative recovery of ethyl acrylate, and treats the black acid residues with an aqueous alkanol mixture. No materials are directly returned to the EA-producing reactor nor to the distillation column which generates the black acid stream. The '834 process thus provides partial recovery of ethanol, EA and AA, but only by an aqueous treatment which is isolated from the reactor of the ethylene-AA process. Other processes employ distillation units (often designated "bleed strippers") to partially recover free AA, BA, and BuOH from reaction bleeds, but to the extent that heavy ends are recovered in that operation, they remain chemically in the higher boiling (heavy end) form and are not transformed to the desired valuable AA, BA, and BuOH forms.

Distillation is commonly used in BA production. For example, U.S. Pat. No. 4,012,439 ('439) describes a continuous process for BA in which a reactor esterification mixture is distilled through an AA separation column to give an overhead mixture of BA, butanol, and water, and, from the column bottom, a concentrated AA stream which is returned to the reactor. While separating the overhead mixture from AA, the '439 process recycles a very high proportion (>97%) of aqueous phase distillate to the head of the AA-separating column. This high proportion of aqueous recycle (i.e. having an aqueous reflux ratio of about 32:1) disadvantageously requires a large column and a large expenditure of energy in returning large volumes of water to the process.

Thus, in the acid-catalyzed production of acrylic acid alkyl esters ("alkyl acrylates"), particularly of BA, there remain significant energy use and reactant recovery problems. There are needs for a process which would recover reactants from their higher boiling, heavy end, adducts formed during the production of acrylic esters, e.g. BA, which would recycle recovered reactants and the ester to the esterification reactor or elsewhere in the process for reuse. Further needs include methods making more efficient use of the water of reaction, both in facilitating distillative separation of acrylic ester from AA and in more efficiently recovering and recycling unreacted AA, particularly if these steps were accomplished with reduced energy use. Meeting one or more of these needs would provide increases in process and/or material use efficiencies. Additionally, if such improved processes led to reduced dibutyl ether (DBE) byproduct in comparison to known processes, even greater process efficiency would result.

We have discovered a high yield process for producing alkyl acrylates, using BA as a preferred example, which achieves these desirable ends. Our new process provides for the recovery of "values," that is, reactants and alkyl acrylate product, from the heavy ends produced in the process. Our new process includes the use of at least one of the following process components: 1. recovering values from a hydrolysis reactor unit ("HRU") fed with a source of heavy ends, as from an esterification reactor; 2. recovering additional values from a cracking reactor preferably used in conjunction with the hydrolysis reactor; and 3. specific to a continuous BA process, distilling by use of an acrylic acid separation column in an efficient new way and providing recovery of BA which is substantially free of AA. Our new process advantageously provides very low levels of DBE in product BA because the esterification reactor is operated under mild temperature and pressure conditions, and at relatively low acid catalyst levels.

Thus, in the broadest use of the hydrolytic recovery component of the invention, there is provided a method of recovering AA, a $C_1$–$C_4$ alkyl acrylate, and a $C_1$–$C_4$ alkanol from heavy ends produced during production of the $C_1$–$C_4$ alkyl acrylate, comprising the steps of:

a) feeding a total aqueous and heavy end feed stream comprising the heavy ends, water, residual acid catalyst, and optionally a strong acid selected from a mineral acid or sulfonic acid, to a hydrolysis reactor maintained at 90° to 140° C., 50 to 1000 mm Hg pressure, and a residence time of 0.5 to 20 hours based on the total aqueous and organic feed stream;

b) distilling an overhead stream containing AA, the $C_1$–$C_4$ alkyl acrylate, the $C_1$–$C_4$ alkanol, and water from the hydrolysis reactor while maintaining a hydrolysis reactor liquid concentration of from 5 to 40 weight % water and at least 1 weight % acid, the acid comprising the residual acid catalyst and the optional strong acid;

c) condensing the overhead stream;

d) separating from the condensed overhead stream an organic phase comprising the $C_1$–$C_4$ alkyl acrylate, the $C_1$–$C_4$ alkanol, and AA, and an aqueous phase comprising primarily water, and AA and the $C_1$–$C_4$ alkanol;

e) removing the separated organic phase;

f) recycling the separated aqueous phase to the hydrolysis reactor; and g) withdrawing from the hydrolysis reactor from 20 to 70 weight %, based on the total aqueous and heavy end feed stream, of a hydrolysis reactor bleed stream.

Specific to BA production, there is provided a method of recovering AA, n-butyl acrylate (BA), and n-butanol (BuOH) from heavy ends produced during acid-catalyzed esterification of AA with BuOH, comprising the steps of:

a) feeding a total aqueous and heavy end feed stream comprising AA, BA, BuOH, water, heavy ends, residual acid catalyst, and optionally a strong acid selected from a mineral acid or sulfonic acid, to a hydrolysis reactor maintained at 90° to 140° C., 50 to 1000 mm Hg pressure, and a residence time of 0.5 to 20.0 hours based on the total aqueous and heavy end feed stream;

b) distilling an overhead stream containing AA, BA, BuOH, and water from the hydrolysis reactor while maintaining a hydrolysis reactor liquid concentration of from 5 to 40 weight % water and at least 1 weight % acid, the acid comprising the residual acid catalyst and the optional strong acid;

c) condensing the overhead stream;

d) separating from the condensed overhead stream an organic phase comprising the BA, the BuOH, and AA, and an aqueous phase comprising primarily water, and AA, and BuOH;

e) removing the separated organic phase;

f) recycling the separated aqueous phase to the hydrolysis reactor; and g) withdrawing from the hydrolysis reactor from 20 to 70 weight %, based on the total aqueous and heavy end feed stream, of a hydrolysis reactor bleed stream.

Another embodiment of the invention provides a method of continuously recovering AA, n-butyl acrylate (BA), and n-butanol (BuOH) from heavy ends produced during acid-catalyzed esterification of AA with BuOH, comprising the steps of:

a) withdrawing continuously a reactor bleed stream from an esterification reactor containing an esterification reaction mixture comprising AA, BA, BuOH, water, heavy ends, and residual acid catalyst, while concurrently distilling AA, BA, BuOH, and water from the esterification reaction mixture;

b) feeding a total aqueous and organic feed stream comprising the reactor bleed stream, water, optionally a strong acid selected from a mineral acid or sulfonic acid, and optionally additional heavy ends, to a hydrolysis reactor maintained at 90° to 140° C., 50 to 1000 mm Hg pressure, and a residence time of 0.5 to 20 hours based on the total aqueous and organic feed stream;

c) distilling an overhead stream containing AA, BA, BuOH, and water from the hydrolysis reactor while maintaining a hydrolysis reactor liquid concentration of from 5 to 40 weight % water and at least 1 weight % acid, the acid comprising the residual acid catalyst and the optional strong acid;

d) condensing the overhead stream;

e) separating from the condensed overhead stream an organic phase comprising BA, BuOH, and AA, and an aqueous phase comprising primarily water, and AA, and BuOH;

f) removing the separated organic phase;

g) recycling the separated aqueous phase to the hydrolysis reactor; and h) withdrawing from the hydrolysis reactor from 20 to 70 weight %, based on the total aqueous and organic feed stream, of a hydrolysis reactor bleed stream.

Additional recovery of valuable reactants is achieved from heavy ends by using a cracking reactor in tandem with the hydrolytic recovery methods described above. That process is carried out with any of the above-described hydrolytic recovery methods by further including the steps of:

a) feeding up to 100% of the hydrolysis reactor bleed stream to a cracking reactor maintained at 90° to 140° C., a pressure of from 20 to 200 mm Hg, and a residence time of 0.5 to 20 hours based on the fed reactor bleed stream;

b) distilling from the cracking reactor a cracking reactor overhead stream comprising AA, the $C_1$–$C_4$ alkyl acrylate, the $C_1$–$C_4$ alkanol, and water while maintaining a cracking reactor liquid concentration of at least 7.5 weight % acid;

c) condensing the cracking reactor overhead stream; and d) recovering from the cracking reactor overhead stream AA, $C_1$–$C_4$ alkyl acrylate, $C_1$–$C_4$ alkanol, and water.

Preferably, the alkyl acrylate is BA. More preferably, the cracking reactor just described is used in tandem with the hydrolytic reactor in a continuous acid-catalyzed process for producing BA.

In a second component of the invention, this relating to continuous production of BA, there is provided a method of continuously recovering n-butyl acrylate (BA) substantially free of AA from an esterification reaction mixture, comprising the steps of:

a) feeding continuously to an esterification reactor AA and BuOH in a molar ratio of from 1 to 1.1 to 1 to 1.7, and an acid catalyst;

b) reacting the AA and BuOH to yield BA in a conversion of at least 60% on AA, and yielding the esterification reaction mixture comprising AA, BA, BuOH, water, heavy ends, and acid catalyst;

c) distilling from the esterification reactor a vaporized mixture comprising AA, BA, BuOH, and water;

d) condensing the vaporized mixture to provide a first condensate comprising an organic phase and an aqueous phase;

e) returning from 0 to 30 percent of the organic phase to an entrainment separator surmounting the esterification reactor; and f) feeding from 70 to 100 percent of the organic phase and from 50 to 100 percent of the aqueous phase to an acrylic acid separation column;

g) distilling from the acrylic acid separation column, at a pressure of from 35 to 800 mm Hg, in an aqueous mode and at an aqueous reflux ratio of 8.5:1 to 17:1, an overhead mixture comprising an azeotropic mixture of butanol, butyl acrylate and water;

h) removing from the distillation column an acrylic acid-rich bottom stream;

i) recycling the acrylic acid-rich bottom stream from the acrylic acid separation column to the esterification reactor;

j) condensing the overhead mixture to provide a second condensate;

k) separating the second condensate into a butyl acrylate-rich organic phase and a separated aqueous phase; and l) removing the butyl acrylate-rich organic phase substantially free of AA.

The recovering of BA substantially free of AA also may be carried out by feeding the vaporized reactor mixture directly to the AA separation column by bypassing the d), e), and f) steps immediately above. When the vaporized mixture is fed directly to the column, the aqueous reflux ratio is tightened to 13:1 to 17:1; all other steps are identical, except there is, of course, no "first condensate."

BRIEF DESCRIPTION OF THE DRAWINGS

In a brief description of the drawings, the process embodying both components of the invention is shown schematically in FIG. 1; FIGS. 1 and 2 are described in greater detail below.

DETAILED DESCRIPTION OF THE INVENTION

Figure 1:
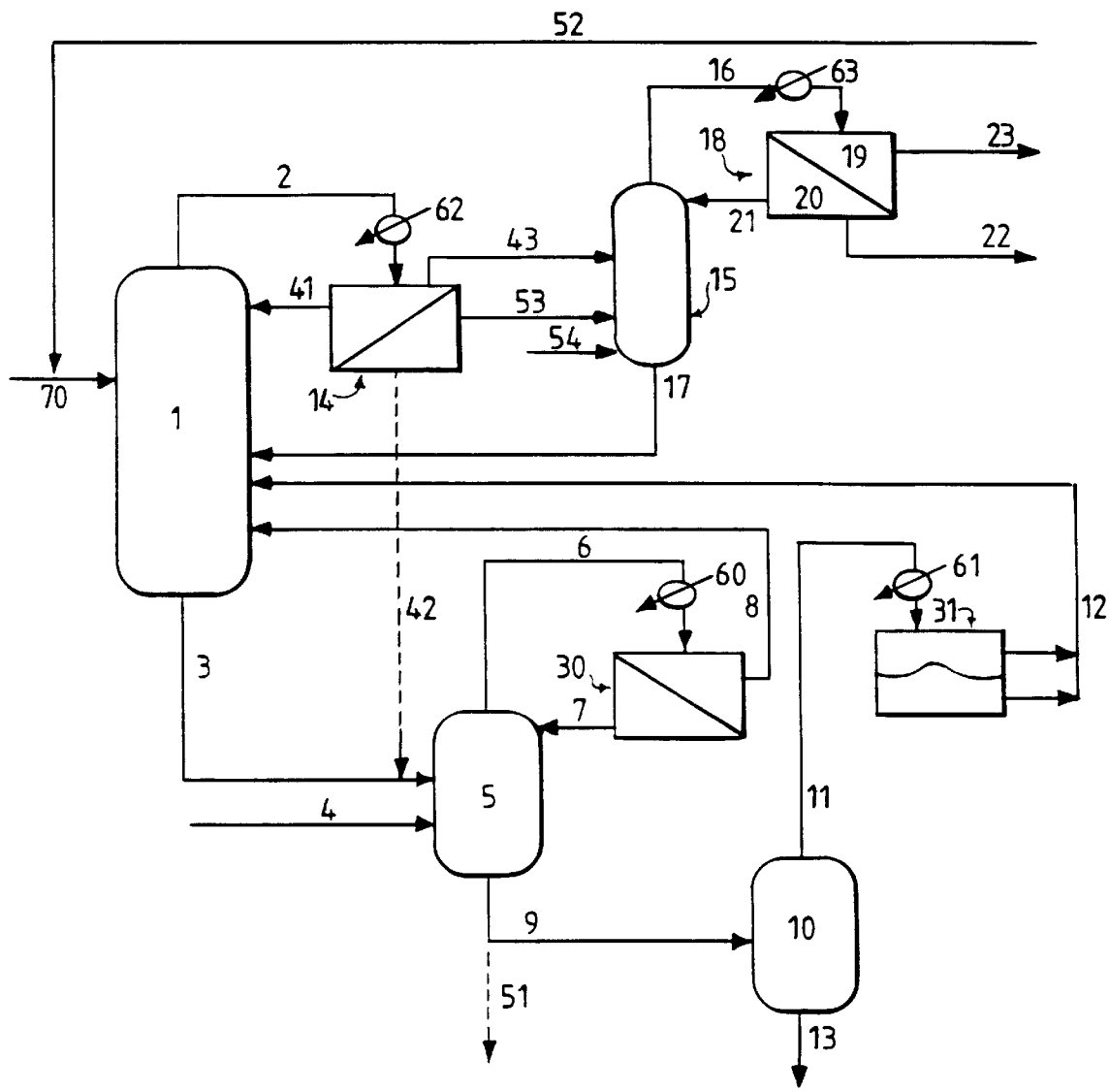
FIG. 1 shows equipment and flow lines, including esterification reactor 1, bleed line 3 to a hydrolysis reactor unit (HRU) 5; and associated streams and lines, particularly line 8 returning organic phase to reactor 1 and line 7 returning aqueous phase to the HRU. Cracking reactor 10 also has associated lines, e.g. for draining and distilling, and providing for returning the condensed overhead stream from separator 31 to reactor 1 via line 12. In a brief description of the drawing relating to the distillation component, FIG. 1 includes line 2 feeding an esterification reactor vaporized mixture (in this embodiment) to a condenser 62 and the condensate to a phase separator 14 and associated lines from the phase separator to the acrylic acid separation column 15 via one or more line 43, 53, and for optionally feeding some of the aqueous phase to the HRU 5 via line 42 and optionally a portion of the organic phase to an entrainment separator surmounting reactor 1 via line 41, when separator 14 is used. Line 54 provides for optional feed of BuOH to the AA separation column. Lines from the acrylic acid separation column include 17, returning the AA-rich bottom stream to reactor 1, and line 16 conveying the distilled overhead mixture through condenser 63 to phase separator 18 and its associated lines, line 21 returning a controlled portion of the aqueous phase 20 to the top of acrylic acid separation column 15, line 22 moving forward a controlled portion of the separated aqueous phase and line 23 carrying forward all of the BA-rich organic phase, 19. Line 52 provides for BA/BuOH return to reactor 1 during subsequent conventional processing and final BA product isolation.

The first component of the invention, the hydrolytic recovery component which recovers values from heavy ends, takes advantage of the known ability of a strong acid, for example, a mineral acid such as sulfuric acid, to catalyze the individual reactions employed: direct esterification, ester hydrolysis, dehydration, and retro-Michael reactions. Thus, catalytic processes in which esters and heavy end hydrolyses occur in a hydrolysis reactor and, in an extended embodiment, dehydration and retro-Michael additions carried out in a cracking reactor, are new efficient methods for recovering, for example, BA, BuOH, and AA values from heavy end components formed during prior reaction in, for this example, a BA esterification reactor. The heavy ends are exemplified in detail for BA production using sulfuric acid catalyst in the reactor and in the HRU; from these examples one skilled in the art would recognize analogous "heavy end" counterparts from producing any of the $C_1$–$C_4$ alkyl acrylates. The $C_1$–$C_4$ alkyl groups may be methyl, ethyl, propyl and iso-propyl, and the butyl isomers, preferably n-butyl. Heavy ends are adducts higher in boiling point than the reactants and, as exemplified here, the butyl acrylate product; they include, for example, acryloxy-propionic acid ("AOPA") and its butyl ester derivative, beta-hydroxy propionic acid and its butyl ester derivative, beta-butoxy propionic acid and its butyl ester derivative, and other non-polymeric adducts of the reactants. In addition, maleic acid and benzoic acid impurities in the acrylic acid and sulfuric acid catalyst are present as maleic acid monobutyl ester, butyl benzoate, and mono-butyl sulfate. Furthermore, the simultaneous removal of BA, BuOH, and AA by way of the distillate streams of both hydrolysis and cracking reactors in a continuous process allows the recovery reactions to proceed beyond equilibrium constraints present in a batch process and thus improve process yields. Another advantage of the hydrolytic recovery component of the invention is that one or more additional heavy end streams may be worked into the hydrolytic recovery process stream, thus providing recovery of additional values.

The following are examples of heavy end materials present in the total aqueous and organic (i.e. heavy ends alone, or mixture of heavy ends, reactants, and product) feed stream which are hydrolyzed in the hydrolysis reactor to afford valuable recoveries of AA and the described alkyl acrylates and alkanols. Alkyl esters of the β-alkyloxy propionates are a common heavy end material. In the beta position of the alkyl esters also may be the hydroxy group instead of an alkyloxy group. β-Acryloxy acid derivatives of the $C_1$–$C_4$ alkyl esters also may be present in the heavy ends; for example, butyl (β-acryloxy) propionate is commonly present in the heavy end materials along with its corresponding acid, in BA production. Also present are the $C_1$–$C_4$ esters of sulfuric acid catalyst which esters are hydrolyzed to sulfuric acid and the corresponding $C_1$–$C_4$ alkanol.

The reactions which take place in the HRU can be generalized by equations 1 and 2, following:

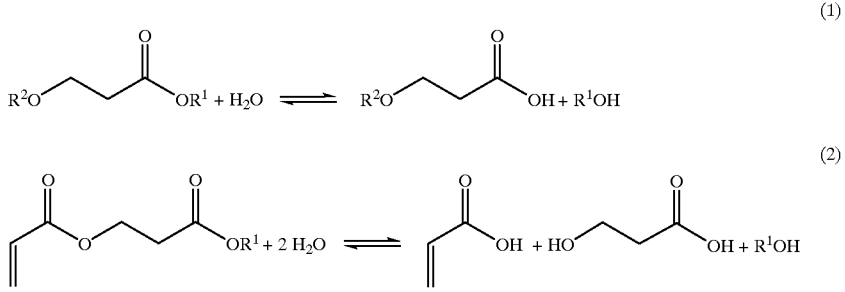

(1)

(2)

Here, $R^1$ is a $C_1$–$C_4$ alkyl group as defined above; $R^2$ is a $C_1$–$C_4$ alkyl group or H. Additionally, saturated and unsaturated esters, such as the $C_1$–$C_4$ alkyl ester of benzoic acid and the $C_1$–$C_4$ alkyl ester of maleic acid as well as $C_1$–$C_4$ alkyl sulfate, can be similarly hydrolyzed to release an equivalent of $C_1$–$C_4$ alkanol. Furthermore, the simultaneous removal of BA, BuOH, and AA via the HRU's distillate stream allows the recovery reactions to proceed beyond equilibrium constraints and improve overall process yields. However, the parent carboxylic acid of several heavy materials cannot be recovered in the HRU and, therefore, an additional recovery scheme is necessary for these materials and is carried out in a cracking reactor.

The reactions which take place in the cracking reactor can be generalized by equations 3 and 4, following, where $R^2$ is as defined above:

(3)

(4)

The conversion of $C_1$–$C_4$ alkyl ester of beta-hydroxy propionic acid, beta-alkoxy propionic acid, and beta-acryloxy propionic acid to the parent acid in the HRU (via ester hydrolysis) is quite beneficial since it is well known that these materials undergo dehydration and retro-Michael addition in acid form. Therefore, under the relatively dry conditions of the cracking reactor, compounds such as beta-n-butoxy propionic acid and beta-hydroxy propionic acid can undergo dehydration resulting in recovery of acrylic acid and butanol. The well known dimer of acrylic acid (AOPA) undergoes cracking to yield 2 moles of acrylic acid. Here again, the continuous removal of products allows the reactions to proceed beyond equilibrium constraints and improve the overall process yield.

Referring to FIG. 1 in the working of the preferred continuous hydrolytic recovery component of the invention in producing BA: esterification reactor bleed stream 3 is fed from esterification reactor 1 to hydrolysis reactor unit ("HRU") 5. The hydrolytic recovery method of any embodiment of the invention may be carried out in a multiplate reactive distillation column or other staged reactor, and preferably is carried out under continuously mixed conditions, as in a continuous flow stirred tank reactor ("CSTR"). By "bleed stream" is meant any process stream which is controllably withdrawn from one vessel to another, such as from a reactor to another reactor or distillation column. Here, the esterification reactor bleed stream 3 contains acid catalyst, water, AA, BA, BuOH, and heavy ends; polymerization inhibitors also may be present. Additional feeds via 4 may include water, and may also include mineral acid, for example, sulfuric acid, or a sulfonic acid such as methane-, benzene-, or toluene-sulfonic acid. The mineral or sulfonic acid is added as required to meet the specified minimal usage level in the HRU. One or more additional streams containing heavy ends from sources other than the esterification reactor also may be added. These feeds may be added by one or more feed lines represented by 4. The additional heavy ends may comprise up to 80 wt. % of the total aqueous and organic feed stream. Sulfuric acid is most preferred for use as both reactor acid catalyst and mineral acid in all embodiments of the invention. The HRU mixture of the described feed streams is maintained in a boiling state under the conditions defined. The residence time of from 0.5 to 20 hours is based on the total aqueous and organic feed stream ("total" meaning the sum of the aqueous and heavy ends and/or reactor bleed streams) fed to the HRU. Preferred residence time is from 0.5 to 5 hrs, and more preferred is 0.5 to 3 hrs. An overhead stream is distilled from the HRU mixture in 6 and condensed, 60, into phase separator 30. The condensed overhead stream separates into an organic phase rich in BA, BuOH and AA, and into an aqueous phase containing primarily (i.e. >50%) water and some BuOH and AA. The separated aqueous phase is returned to the hydrolysis reactor 5 via 7 and the separated organic phase, as stream 8, is returned in this embodiment to the esterification reactor 1, thus recovering valuable BA, BuOH, and AA for subsequent reaction and product recovery. The separated organic phase also may be fed to separator 14 for recovery by way of line 43 and distillation through 15. An undistilled residue, from 20 to 70 wt. % of the total aqueous and organic feed stream, is bled as the hydrolysis reactor bleed stream 9 from the hydrolysis reactor for further handling (e.g. as a waste stream by line 51 or, preferably, as feed to a cracking reactor by line 9.)

A preferred embodiment provides additional recovery of AA, BA and BuOH. As shown in FIG. 1, the hydrolysis reactor bleed stream 9 is fed to a cracking reactor 10 and treated as now described. The cracking reactor may be of construction similar to that of the HRU and is, preferably, a CSTR. The cracking reactor liquid is maintained at least at 7.5 wt. % mineral acid, preferably sulfuric, and also contains a mixture of acrylic acid, BuOH, BA, some heavy ends and residual polymerization inhibitors. Additional mineral or sulfonic acid may be added to the cracking reactor liquid (feed line not shown). The cracking reactor mixture is maintained in a boiling state under the previously described cracking conditions while an overhead stream is distilled from the cracking reactor via line 11 and condensed via 61 to separator 31. The condensate contains an organic distillate stream containing AA, BA and BuOH, and also some water; all of the condensed overhead stream is returned as stream 12 to the esterification reactor, thus providing additional recovery of valuable AA, BA, and BuOH. The cracking reactor residue stream 13 is drained off for further handling, generally as waste. Preferred and more preferred cracking reactor residence times are the same as described for the HRU, namely, 0.5–5 hrs and 0.5–3 hrs, respectively.

The HRU may be a multi-plate reactive distillation column so long as sufficient number of plates are incorporated to provide specified residence time. When a reactive distillation column is employed as an HRU, a separate cracking reactor unit may not be needed to achieve acceptable values recoveries. Under most production conditions it is preferred to use the cracking reactor in tandem with a hydrolytic reactive distillation column, similar to its use when the HRU is a CSTR. One disadvantage of a reactive distillation column over a CSTR is that occasional build-up of solids on the column trays may require undesirable down time for column cleaning.

Addition of one or more additional feed streams to the esterification reactor bleed stream or directly to the hydrolysis reactor permits additional recovery of AA, and for example, BA, and BuOH, through the processes occurring in the hydrolysis reactor and, when used, the cracking reactor. The liquid in the hydrolysis reactor has at least 5 wt. % water for efficient operation; preferably the HRU liquid contains from 9 to 18 wt. %, more preferably from 10 to 16 wt. % water, in order to achieve efficient hydrolysis rates under nominal thermal and pressure conditions and practical equipment size. Water content is maintained by a combination of returning the entire condensed and separated aqueous stream in line 7 to the hydrolysis reactor and by adding additional water from other sources, e.g. by lines 4 and 42, to compensate for water losses to organic distillate and the HRU bleed stream. Water addition from the distilled aqueous phase from the esterification reactor, by line 42, is a preferred source of water in the continuous BA process. In order to maintain efficient dehydration and retro-Michael reaction rates in the cracking reactor, the cracking reaction mixture should have an aqueous content lower than that of the HRU mixture. Water contents typically below 5 wt. %, preferably below 1 wt. %, are achieved by operating the cracking reactor as a single stage unit, that is, by continuously distilling from the cracking reactor any water carried over from the hydrolysis reactor bleed stream and any additional water generated from cracking reactions.

Additional acid may be added to the recovery units as necessary to achieve practical reaction rates; preferably acid is added by way of one or more of the feed streams. "Residual acid catalyst" is acid catalyst which remains present as acid in the esterification reactor bleed stream and thus is carried forward to the HRU. In the HRU, acid concentration is preferably in the range of 3.5 to 15 wt. %, and most preferably is 5 to 8 wt. %. Acid concentration in the cracking reactor is typically in the range of 7.5 to 20 wt. %, and could be higher, e.g. up to 50%. Acid concentration preferably is from 10 to 13 wt.%, particularly for BA production. The amount of heavy ends in the esterification reactor bleed stream may vary but typically is in the range of from 10 to 50 wt. % of the combined total of the aqueous and organic-containing feed stream.

Hydrolysis reaction temperatures range from 90° to 140° C., and are preferably from 105° to 125° C. for efficient hydrolysis rates; temperatures greater than 140° C. may lead to thermally induced polymerization of alkyl acrylates and of acryloxy-bearing heavy ends, resulting in undesired product loss. The residence time required for HRU hydrolysis reaction is preferably from 0.5 to 5 hours, more preferably from 0.5 to 3 hours, shorter times being more economical. Lower temperatures, and the presence of water, also favor reduced DBE formation. Cracking reactor temperatures range from 90° to 140° C., preferably from 110° to 125° C.; cracking pressures typically range from 20 mm Hg to 200 mm Hg, although higher pressures, up to 800 mm Hg may be used. The residence time for dehydration and other reactions in the cracking reactor under these conditions is preferably from 0.5 to 3 hours. For the continuous production of BA, values recoveries are maximized with two CSTR reactors in tandem, one the HRU and the other the cracking reactor.

In order to prevent polymerization, an effective amount of one or more polymerization inhibitor may be added at any step in any component of the process. An esterification reactor process stream typically contains sufficient inhibitor to prevent polymerization in the HRU and cracking reactor. If additional inhibitor addition is required, any of a large number of known inhibitors may be used, for example, hydroquinone, the mono-methyl ether of hydroquinone, butylated hydroxy anisole, naphthaquinone, anthranil, and derivatives of these.

The second component of the invention, the distillative component, further improves known methods of distilling crude BA and provides BA substantially free of AA by more efficiently handling distillate and aqueous reflux. Specifically, the new distillative method provides BA in the BA-rich stream containing less than 2,000 ppm of AA for moving forward for subsequent conventional isolation. The method also provides an AA recycle stream containing negligible BA, specifically providing an AA recycle stream (the bottom, AA-rich phase) containing less than 10 ppm, preferably less than 5 ppm, of BA. In generating the crude BA for the new distillative component of the invention, AA and BuOH are initially fed, line 70, along with acid catalyst, to an esterification reactor in a molar ratio of AA to BuOH in the range of 1:1.1 to 1:1.7, preferably 1:1.25 to 1:1.45, and reacted to a conversion on AA of from 60 to 95%, preferably 75 to 85%, using an acid catalyst of the mineral or sulfonic acid type previously described, or a strong acid ion exchange resin; preferably sulfuric acid is used. The reactant ratio and BA conversion provide a crude BA stream which may be processed to provide stable "aqueous mode" operation (discussed in detail below) of the acrylic acid separation column. Reactor contents are maintained in a boiling state during continuous distillation of the vaporized mixture of AA, BA, BuOH and water.

Referring to FIG. 1, vaporized mixture by line 2 from the reactor 1 is condensed, 62, and fed to phase separator 14 (in this embodiment) to provide the first condensate. Alternatively, the vaporized mixture may be fed directly to the column 15 for distillation as described above. An entrainment separator, not shown, also may be mounted on the reactor, to reduce or eliminate entrainment of acid catalyst in the vaporized mixture, thus reducing downstream corrosion potential. Phase separator 14 is particularly useful when an entrainment separator is employed, assuring an organic reflux layer return to the entrainment separator, and also as a means for providing optional aqueous stream 42 to an HRU. The first condensate comprises an organic phase primarily (i.e. more than 50%) of BA and BuOH, with some AA, and an aqueous phase primarily of water, with some BuOH and AA. All of both phases may be fed to the acrylic acid separation column 15 by one or more line, e.g. 43, 53, or, optionally, up to 50 wt. % of the aqueous phase may be diverted via line 42 to the hydrolytic recovery unit 5 (when preferably used). Additional butanol optionally may be fed to the column via line 54. An overhead azeotropic mixture is distilled from the acrylic acid separation column, under the pressure, temperature, and aqueous reflux conditions previously described, and condensed by line 16 and condenser 63 into phase separator 18, yielding a second condensate comprising BA-rich organic phase 19 and aqueous phase 20. By "BA-rich," or "AA-rich," is meant that BA, or AA, is the primary (>50 wt. %) organic component of a given phase. Concurrently, an AA-rich bottom stream, containing negligible BA, is withdrawn from the bottom of the acrylic acid separation column and by line 17 returned to the esterification reactor 1. The amount of the recycled aqueous stream 21 is adjusted to provide at least an 8.5:1 minimum aqueous reflux ratio in the AA separation column 15 in order to maintain the column in the critical "aqueous mode" operation. In the aqueous mode operation, the AA separation column performs a surprisingly effective separation of AA from the BA-containing feed stream (i.e. the first condensate stream or the vaporized mixture stream fed to the column), resulting in low AA losses in the BA distillate and consequently higher BA yield, as shown in further detail below. A small portion, 6 to 11 wt. % of the separated aqueous phase 20, typically is fed forward as stream 22, along with the forward feeding of the BA-rich organic phase 19 in stream 23 for subsequent conventional isolation of final product BA. Conventionally, the aqueous reflux ratio is defined as the ratio of aqueous flow returned to the aqueous flow taken forward, here the ratio of aqueous flow in 21 to that in 22. Maintaining the specified ratio is critical to the efficient operation of the acrylic acid separation column in the invention.

The acrylic acid separation column may have from 20 to 50, preferably 30 to 40, trays and typically is equipped with a bottom reboiler loop (not shown) and an overhead distillate line 16 through condenser 63 to phase separator 18. The first condensate feed typically is fed at about the 10th tray in a 40 tray column, numbered from the column bottom. If optionally used, added BuOH typically is fed at the 8th or 9th tray. The column operates within the limits described previously, and preferably at a pressure of from 90 to 135 mm Hg corresponding to a preferable bottom temperature of from 80° to 85° C. The aqueous reflux ratio during distillation of the overhead mixture is preferably from 8.5 to 12.5 and most preferably from 9.5 to 10.5. The flow rate of the column bottom stream in 17 is adjusted to exceed the amount of AA in the column feed by 5 to 25 wt. % to ensure that all AA remains in the column bottom. Stream 17 typically contains 5 to 20 wt. % water, the balance being primarily AA and AOPA. The acrylic acid separation column, run as described, provides BA substantially free of AA (<2,000 ppm) and an AA bottom stream containing negligible (<10 ppm) BA.

One of the unexpected findings in the modeling and subsequent demonstration of the acrylic acid separation column use was that two steady states existed at the same operating conditions (that is, at the same feed rate, feed composition, aqueous reflux flow rate, and bottom flow rate). One steady state, referred to above as the "aqueous mode," is critical to obtaining the very low levels of AA in the BA-rich phase and of BA in the AA-rich bottom stream as previously described. In the aqueous mode the acrylic acid separation column runs relatively "cool," there are substantial amounts of water in the liquid on all trays, water is present in the bottom stream, and there is negligible BA in the bottom stream. In surprising contrast, however, there exists at the same conditions (that is, at the same feed rate, feed composition, aqueous reflux flow rate, and bottom flow rate) a second mode, the "organic mode," which is undesirable. In the organic mode, the acrylic acid separation column runs about 30–35° C. hotter than in the aqueous mode, considerable amounts (>10 wt %) of BA are found in the bottom stream, and the concentration of AA in the overhead mixture of BA is at least an order of magnitude larger than the maximum of 2,000 ppm AA achieved via aqueous mode operation. Also in the undesirable organic mode, the column not only is hotter than in the aqueous mode, but all the water is concentrated in the top several trays and the bottom stream is substantially dry. Examples 1–6 and the below-described modeling studies provide further detail of the unexpected finding of these modes and the rationale behind running the acrylic acid separation column as defined.

Finally, there is provided a most preferred continuous process, employing all components of the invention in combination, for producing BA substantially free of acrylic acid (AA), and for recovering AA, BA, n-butanol (BuOH) and water from an esterification reactor mixture containing AA, BA, BuOH, water, heavy ends, and acid catalyst, which comprises the following steps:

a) feeding to an esterification reactor AA and BuOH, in a molar ratio of from 1 to 1.1 to 1 to 1.7, and the acid catalyst;

b) Reacting the AA and BuOH to yield BA in a conversion of at least 60% on AA, and yielding the esterification reaction mixture comprising AA, BA, BuOH, water, heavy ends, and acid catalyst;

c) withdrawing a reactor bleed stream from the continuously converting esterification reactor mixture while concurrently distilling AA, BA, BuOH and water from the esterification reaction mixture;

d) feeding a total aqueous and organic feed stream comprising the reactor bleed stream, water, optionally a strong acid selected from a mineral acid or sulfonic acid, and optionally additional heavy ends, to a hydrolysis reactor maintained at 90° to 140° C., 50 to 1000 mm Hg pressure, and a residence time of 0.5 to 20 hours based on the total aqueous and organic feed stream;

e) distilling an overhead stream containing AA, BA, BuOH, and water from the hydrolysis reactor while maintaining a hydrolysis reactor liquid concentration of from 5 to 40 weight % water and at least 1 weight % acid, the acid comprising the acid catalyst and the optional strong acid;

f) condensing the overhead stream;

g) separating from the condensed overhead stream an organic phase comprising BA, BuOH, and AA, and an aqueous phase comprising primarily water, and AA, and BuOH;

h) feeding the separated organic phase to the esterification reactor;

i) feeding the separated aqueous phase to the hydrolysis reactor;

j) withdrawing from the hydrolysis reactor from 20 to 70 weight %, based on the total aqueous and organic feed stream, of a hydrolysis reactor bleed stream;

k) feeding up to 100% of the hydrolysis reactor bleed stream to a cracking reactor maintained at 90° to 140° C., a pressure of from 20 to 200 mm Hg, and a residence time of 0.5 to 20 hours based on the fed reactor bleed stream;

l) distilling from the cracking reactor a cracking reactor overhead stream comprising AA, BA, BuOH, and water while maintaining a cracking reactor liquid concentration of at least 7.5 weight % acid;

m) condensing the cracking reactor overhead stream;

n) recycling to the esterification reactor the condensed cracking reactor overhead stream comprising AA, BA, BuOH, and water;

o) distilling from the esterification reactor, concurrently with above steps c) through n), a vaporized mixture comprising AA, BA, BuOH, and water;

p) condensing the vaporized mixture to provide a first condensate comprising an organic phase and an aqueous phase;

q) returning from 0 to 30 percent of the organic phase to an entrainment separator surmounting the esterification reactor; and r) feeding from 70 to 100 percent of the organic phase and from 50 to 100 percent of the aqueous phase to an acrylic acid separation column;

s) distilling from the acrylic acid separation column, at a pressure of from 35 to 800 mm Hg, in an aqueous mode and at an aqueous reflux ratio of 8.5:1 to 17:1, an overhead mixture comprising an azeotropic mixture of butanol, butyl acrylate and water;

t) removing from the distillation column an acrylic acid-rich bottom stream;

u) recycling the acrylic acid-rich bottom stream from the acrylic acid separation column to the esterification reactor;

v) condensing the overhead mixture to provide a second condensate;

w) separating the second condensate into a butyl acrylate-rich organic phase and a separated aqueous phase; and x) removing the butyl acrylate-rich organic phase substantially free of AA.

This method described immediately above also may be carried out wherein steps p), q), and r) are bypassed and 100 percent of the vaporized mixture is fed directly to the acrylic acid separation column of step s) and distilled thereafter as described. When the vaporized mixture is fed directly to the column, the aqueous reflux ratio is tightened to 13:1 to 17:1; all other steps are identical, except there is, of course, no "first condensate."

In the continuous methods described immediately above, the acid catalyst may be selected from sulfuric acid, a sulfonic acid, preferably methane-, benzene-, and toluene-sulfonic acid, or a strong acid ion exchange resin. Sulfuric acid is preferred for use both as the acid catalyst and as the optionally added mineral acid. A preferable pressure range for carrying out the distillation in the AA separation column is from 90 mm to 135 mm Hg. A preferred aqueous reflux ratio is, again, from 8.5 to 12.5. The total aqueous and organic feed stream may be fed either to a hydrolysis reactor which is a multi-plate reactive distillation column or, preferably, to a CSTR, as previously described, thus providing hydrolytic reaction under continuously mixed conditions. The additional heavy ends here also may comprise up to 80 wt. % of the total aqueous and organic feed stream.

Returning to FIG. 1, streams of 20 and 19, are taken forward in 23 or separately, as 22 and 23, and product BA is then isolated by conventional means. Thus, the process from this point forward may be completed conventionally, for example, by feeding streams 22 and 23, to a separator where the stream is caustic-neutralized and any resulting AA salt extracted by water. The AA-free organic phase is then dehydrated through a distillation column, removing final traces of water. In a next column unreacted BuOH is recovered from the overhead as its azeotrope with BA for recycle to the esterification reactor (stream 52), and passing the bottom stream, containing substantially pure BA and inhibitors, to a product final distillation column. In this final column, pure BA is distilled overhead in a conventional manner and a bleed stream containing process inhibitors is removed from the bottom for reuse. Representative purity of the BA obtained from the process just described typically exceeds 99.8% BA.

EXAMPLES

General

Materials

AA, crude and pure n-butyl acrylate (BA), n-butanol (BuOH), and heavy end streams were obtained from plant production streams where indicated and were of the quality/purity indicated. Commercial polymerization inhibitors were used as purchased at levels indicated and included hydroquinone (HQ), HQ methyl ether (MEHQ), and phenothiazine (PTZ). Heavy end components in the Examples include the following materials: AOPA, butyl β-butoxy-propionate ("BBBP"), butyl β-hydroxy-propionate ("BBHP"), butoxy AOPA ("BAOPA"), butyl maleate and DBE.

Figure 2:
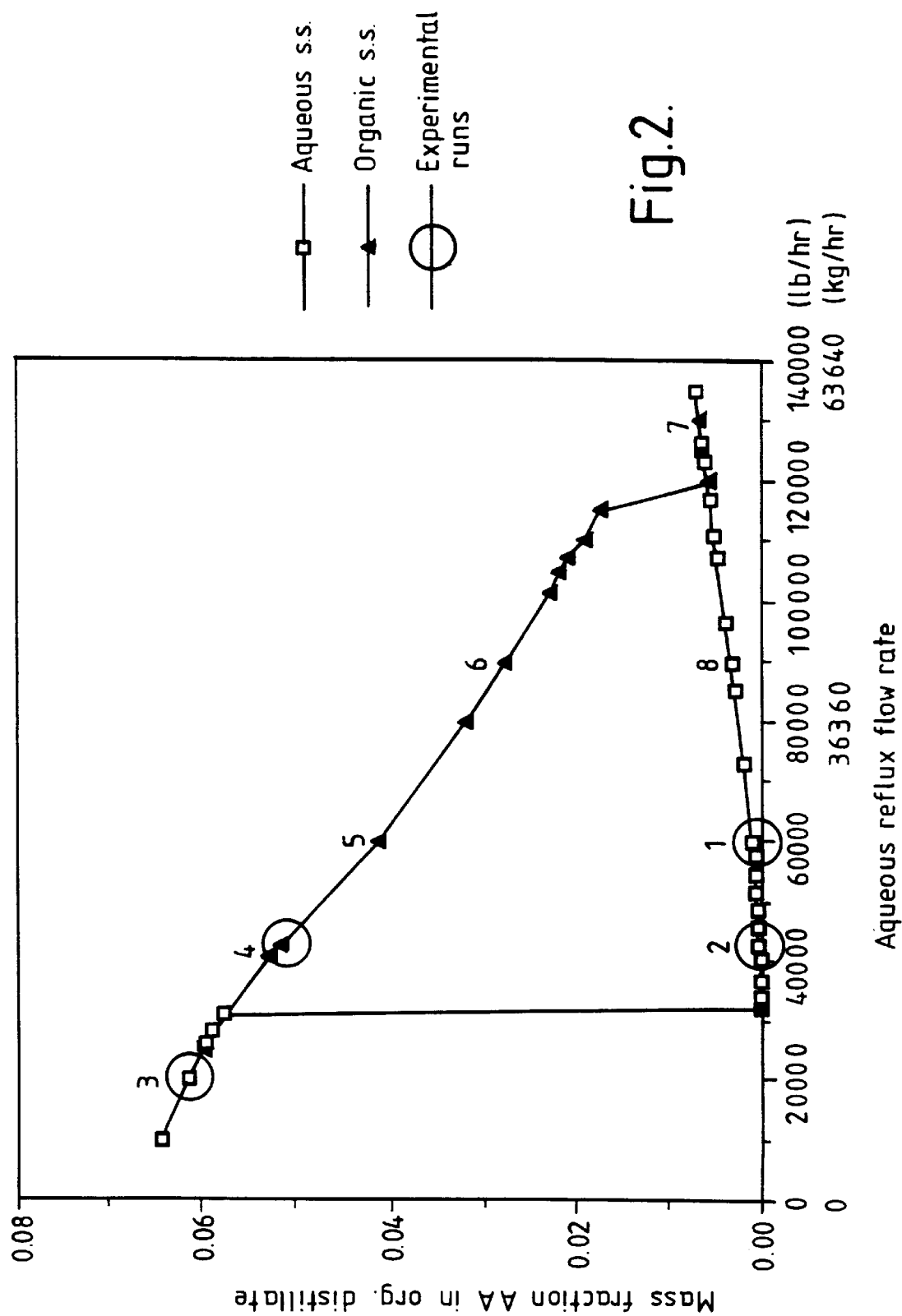
FIG. 2 is a graph of the amount of residual AA in organic distillate obtained by distilling through the acid separation column versus the aqueous reflux flow rate, as obtained under conditions described below.

Abbreviations: These include, in addition to those already defined, the following terms: additional (add'l); aqueous (aq.); Comparative (Comp.); Example (Ex.); Figure (Fig.); gram (g); grams per hour (g/hr); kilogram (Kg); hour(s) (hr(s)); heavy ends or heavy end streams ("heavies"); weight (wt.); millimeters of mercury pressure (mm Hg); millimoles (mmoles or mm); pounds (lbs); vaporized mixture (vap. mixt.); round bottom flask (r.b. flask); less than (<); more than (>); point (pt.); steady state (s.s.). In FIG. 2, data points are abbreviated as follows: open box points are in the aqueous s.s. (mode), triangles are in the organic s.s., and circled data points are experimental/example runs as numbered.

Analyses

Standard methods were used for determination of water; monomer, BuOH, and residual impurity and heavy end levels were determined by gas/liquid chromatography (GLC) on a Varian Model 3700 chromatograph, using flame ionization detection. Sulfuric acid determinations were obtained using an Orion Research Ion analyzer pH probe and alcoholic tetrabutylammonium hydroxide titrant. Unless otherwise noted, $H_2SO_4$ concentrations given in examples are these titrated values. Percentages are in wt. %, unless otherwise indicated.

Values Recoveries

Recovered "values" were calculated and measured as follows from representative heavy ends produced, for example, in BA production. Since all heavy ends related to BA production ultimately are derived from AA and BuOH, the values recovery data were calculated to reflect the recovery of these reactants, even though some recovery is in the form of product BA. For example, 100 moles of BBBP contains the equivalent of 100 moles of acrylic acid and 200 moles of BuOH. Similarly, 100 moles of BAOPA contains the equivalent of 100 moles of BuOH and 200 moles of AA. The "heavies mixture" (which is residue unaccounted for) is assumed, for weight calculation purposes, to be a 1:1 molar mixture of acrylic acid and BuOH with a molecular weight of 146 g/mole. BA monomer contains equivalent molar amounts of AA and BuOH. So-called "free" values are simply the same values in "free" (not incorporated as heavy end) form. Following is a list of BuOH and AA values for representative, characterized heavy ends from exemplified BA esterification reaction.

| Component | Values |
| --- | --- |
| butyl-β-butoxy propionate (BBBP) | 2 BuOH, 1 AA |
| butyl-β-hydroxy propionate (BBHP) | 1 BuOH, 1 AA |
| butyl-acryloxypropionate (BAOPA) | 1 BuOH, 2 AA |
| Acryloxypropionic Acid (AOPA) | 2 AA |
| n-butyl maleate | 1 BuOH |
| Butylhydrogen sulfate | 1 BuOH |
| Heavies Mixture | 1 BuOH, 1 AA |

Process Yield

Process yield was calculated in the following manner. The AA and BuOH present in any additional streams fed to the HRU were treated in yield calculations as if they were fresh (i.e., raw material) AA and BuOH as fed to the esterification reactor. The BA monomer present in additional streams fed to the HRU was treated in yield calculations as if it were recycled BA from a downstream separation (i.e., recycled or supplemental streams); i.e. no yield increment was credited for any recycled BA. The yield on AA or BA can, therefore, exceed 100% when values (as described above) were recovered from the HRU- and HRU/cracker-treated heavy end streams, as described. Thus, in yield calculation summary:

$$\% \text{ Yield of BA, based on AA} = \frac{\text{mole BA (vap. mixt.)} - \text{mole BA (recycled)} - \text{mole BA (add'l streams)}}{\text{mole AA (fresh to reactor)} + \text{mole AA (add'l streams)}}$$

and $$\% \text{ Yield of BA, based on BuOH} = \frac{\text{mole BA (vap. mixt.)} - \text{mole BA (recycled)} - \text{mole BA (add'l streams)}}{\text{mole BuOH (fresh to reactor)} + \text{mole BuOH (add'l streams)}}$$

Equipment

In the following Examples, HRU 5 was a 1 liter 4-neck r.b. flask equipped with a stirrer, water cooled distillation head having a take-off port leading to a 250 ml fraction cutter, phase separator 30. The HRU further was equipped with feed inlet ports 3 and 4 for reactor bleed stream and heavy end stream and other stream additions; a Hastelloy dip tube of 6 mm O.D. connected by a line, 9, to cracking reactor 10 (when used) or to a bleed reservoir by line 52. The HRU was heated with a heating mantle and was mechanically stirred. The various feed and reflux and bleed streams were pumped into and from the reactor from glass feed funnels using metering pumps. HRU thermal control was regulated by an electronic temperature controller attached to a calibrated thermocouple. All process stream lines exposed to streams containing sulfuric acid were constructed of Hastelloy C™ or poly-tetrafluouroethylene (PTFE).

The cracking reactor 10 consisted of a 500 ml flask configured similarly to the HRU regarding temperature control and process stream lines. Bleed stream inlet 9 from the HRU fed the cracking reactor via feed port and pump. Receiver 31 was a 125 ml fraction cutter.

The acrylic acid separation columns are described in specific Examples.

All percentages are by weight, based on the weight of the mixture in which a stated component is contained, unless otherwise indicated.

Modeling Experiments for the Acrylic Acid Separation Column

Modeling studies were performed using "Aspen Plus,"™ an advanced flowsheet simulator from Aspen Technology, Inc. All data points were obtained using an "Aspen" column model which had 13 theoretical trays plus reboiler and decanter and operated at an overhead pressure of 75 mm Hg. The feed tray was the 4th theoretical tray from the bottom; the column bottom stream was sized to contain 90 wt % AA and 10% water during aqueous operation. FIG. 2 shows the two "steady states" (that is, the desired "aqueous" and the undesirable "organic" modes, described previously) of the acrylic acid separation column for the feeds shown in Table 1, corresponding to a reactor conversion of AA to BA of 80% at a molar ratio of AA to BuOH of 1 to 1.35. The data of FIG. 2 are plotted in concentration of AA in the organic distillate as a function of the aqueous reflux flow rate in the column.

The simulations indicated that the minimum aqueous reflux flow rate needed to operate the acrylic acid separation column at the desired aqueous steady state with the feed of Table 1A was approximately 15546 kg (32000 lbs)/hr. The location of the aqueous/organic transition was estimated by recognizing that the separation of BA and AA in the AA separation column is achieved through azeotropic distillation of BA using water as an azeotroping agent. Tables 1A and 1B below illustrate how the minimum amount of water necessary to azeotrope all the BA in the acrylic acid separation column feed was calculated. The first azeotrope to act in the column is the lowest-boiling BA/butanol/water ternary azeotrope which at a pressure of 100 mm Hg boils at 46.4° C. and contains 36.0% BA, 26.4% BuOH, and 37.6% water. This azeotrope depletes the butanol in the feed and takes 10429 kg (22944 lbs)/hr of BA overhead out of a total of 20315 kg (44692 lbs)/hr present in the feed. The amount of water needed to satisfy this first azeotrope exceeds the amount in the feed by 8198 kg (18036 lbs)/hr. Once butanol has been depleted, the next lowest-boiling azeotrope acting in the column is the BA/water binary azeotrope which at a pressure of 100 mm Hg boils at 47.6° C. and contains 61.0% BA and 39.0% water. This second azeotrope takes the remaining 9885 kg (21748 lbs)/hr of BA overhead using 6320 kg (13904 lbs)/hr of water to satisfy the azeotrope composition. The combined analysis of the two azeotropes shows that the total amount of water needed to azeotrope all the BA in the feed exceeds the amount present in the aqueous feed by 6320 kg (31940 lbs)/hr. This corresponds to the minimum amount of water that must be supplied via the aqueous reflux to take all the BA overhead and thus achieve aqueous mode operation. Excellent agreement is shown between this estimate and the location of the aqueous/organic transition predicted by the data in FIG. 2.

TABLES 1A and B

Modeling Feed Conditions and Calculations

1A: Acrylic Acid Separation Column Feed for Modeling Conditions, Calculated at 80% Conversion/AA:BuOH Ratio 1:1.35

| Component | Modeling Column Feed Kg (lbs)/hr | wt % |
|---|---|---|
| AA | 2693 (5925) | 8.1 |
| BuOH | 7648 (16826) | 22.9 |
| BA | 20315 (44692) | 60.9 |
| H2O | 2695 (5928) | 8.1 |
| Total | 33351 (73371) | 100.0 |

1B: Calculation of the Minimum Water Required to Azeotrope All BA in the Feed of Table 1A Under Modeling Conditions

| Comp. | Feed per hour kg (lbs) | 1st Azeotrope (BA/BuOH/H2O) per hour kg (lbs) | wt % | Residual 1[1] per hour kg (lbs) | 2nd Azeotrope (BA/H2O) per hour kg (lbs) | wt % | Residual 2[2] per hour kg (lbs) |
|---|---|---|---|---|---|---|---|
| BA | 20315 (44692) | 10429 (22944) | 36.0 | 9885 (21748) | 9885 (21748) | 61.0 | 0 0 |
| BuOH | 7648 (16826) | 7648 (16826) | 26.4 | 0 0 | 0 0 | 0.0 | 0 0 |
| H2O | 2695 (5928) | 10893 (23964) | 37.6 | −8193 (−18036) (Note 3) | 6320 (13904) | 39.0 | −14518 (−31940) (Note 3) |

Notes:
[1]Residual 1 is the Feed of Table 1A reduced by the 1st Azeotrope components.
[2]Residual 2 is Residual 1 reduced by the 2nd Azeotrope components.
3. Water required to achieve the azeotropic composition of the respective azeotropic distillations, showing deficits by the amount indicated.

1B: Calculation of the Minimum Water Required to Azeotrope All BA in the Feed of Table 1A Under Modeling Conditions

| Comp. | Feed per hour kg (lbs) | 1st Azeotrope (BA/BuOH/H2O) per hour kg (lbs) | wt % | Residual 1[1] per hour kg (lbs) | 2nd Azeotrope (BA/H2O) per hour kg (lbs) | wt % | Residual 2[2] per hour kg (lbs) |
|---|---|---|---|---|---|---|---|
| BA | 20315 (44692) | 10429 (22944) | 36.0 | 9885 (21748) | 9885 (21748) | 61.0 | 0 0 |
| BuOH | 7648 (16826) | 7648 (16826) | 26.4 | 0 0 | 0 0 | 0.0 | 0 0 |
| H2O | 2695 (5928) | 10893 (23964) | 37.6 | −8193 (−18036) (Note 3) | 6320 (13904) | 39.0 | −14518 (−31940) (Note 3) |

Notes:
[1]Residual 1 is the Feed of Table 1A reduced by the 1st Azeotrope components.
[2]Residual 2 is Residual 1 reduced by the 2nd Azeotrope components.
[3]Water required to achieve the azeotropic composition of the respective azeotropic distillations, showing deficits by the amount indicated.

The modeling results presented here correspond to a particular feed to the acrylic acid separation column. However, the same analysis can be applied to any column feed, corresponding to any particular set of reactor conditions, to estimate the minimum aqueous reflux requirement in the column. The ability to accurately predict the minimum water requirement for the acrylic acid separation column based on feed composition alone allows the selection of an operating reflux ratio that minimized the heat duty and diameter of the column while ensuring stable operation in the desired aqueous mode.

In the modeling, it was possible to control which steady state, aqueous or organic, the column operated at by starting a run at an extreme point (i.e., very high reflux rates for aqueous steady state or very low reflux rates for organic steady state) where only the targeted steady state exists, and then moving along the branch, either by decreasing or increasing, respectively, the reflux flow rate until the targeted point of operation was reached. This was achieved through examination of the sensitivity of the process to key variables; in this study, the aqueous reflux flow rate was examined. The two steady state branches of FIG. 2 were obtained by performing two sensitivity studies in the program. In the first study, the aqueous reflux flow rate was started at a very high end of 61364 kg (135000 lbs)/hr (a reflux ratio of about 40, using 1591 kg (3,500 lbs)/hr as the aqueous feed forward rate) and gradually decreased to a very low 4545 kg (10000 lbs)/hr. (a reflux ratio of about 3). This study generated the lower, "aqueous branch" of FIG. 2 which represented the desired aqueous mode where the levels of AA in the organic distillate are very low. (In this program, the lowest level of AA in the distillate (27 ppm) was achieved with the minimum amount of reflux (ca. 15454 kg (32000 lbs)/hr. a reflux ratio of about 9, indicated to run the column in the desired steady state mode.) When the reflux flow rate became too low, the column became inoperable in an aqueous mode and, at ca. 14090 kg (31000 lbs)/hr of reflux, a sudden and very large increase in the distillate AA level occurred. Below 14090 kg (31000 lbs)/hr, the column operated only in the organic mode and the two modes converged to a single solution.

In a second sensitivity study, the aqueous reflux flow rate was started at the low end, at 4545 kg (10000 lbs)/hr, and gradually increased to ca. 61364 kg (135000 lbs)/hr. This study generated the upper, "organic branch" in FIG. 2 and represented the undesired organic mode where the levels of AA in the organic distillate are much higher, as indicated. Moving successively along this branch (points 4–7) to above ca. 54545 kg (120000 lbs)/hr where there is enough water to force the column into aqueous mode of operation, both branches converged to a single aqueous steady state. Within the aqueous branch, the operating region in this simulated study leading to BA having substantially no AA (a target of 2,000 ppm, preferably <1000 ppm,AA), is a small region in the bottom aqueous branch of FIG. 2. The program also predicted high levels of BA (e.g. 23–74 wt. %) in the bottom stream when the column ran in the organic mode. Recycle of BA to the esterification reactor is undesirable because it depresses the rate of conversion of AA and BuOH.

In subsequent modeling of the two steady states in the AA separating column, it was determined that bypassing the reactor condenser and phase separator 14 and feeding a vaporized mixture directly to the column had the advantage of reducing the steam duty requirement of the column. However, because the water in the feed is already vaporized, it is essentially unavailable to form an azeotrope with BA and more reflux water is required to make up for this deficiency. For a vapor feed to the column, the aqueous/organic transition point in FIG. 2 moves toward the right by the amount of water in the feed, and the aqueous reflux ratio range for aqueous-mode operation is tightened to 13:1 to 17:1.

Modeling also showed that refluxing any portion of the organic phase is detrimental to column operation because any BA and butanol returned to the column via an organic reflux will simply need to be removed again by azeotropic distillation with additional water. In addition, AA in the organic reflux is returned to the column at the very top, leaving no trays to rectify this AA contribution out of the overhead vapor. These factors increase the minimum amount of water necessary to operate in the aqueous mode, reduce the width of the aqueous operating window, and raise the minimum levels of AA that can be achieved in the distillate.

Vapor-liquid equilibrium (VLE) data indicate that butanol has the effect of depressing the volatility of AA. In accordance with the VLE data, modeling shows that column feed streams that are rich in butanol give distillate streams that are low in AA. Therefore, low conversions and high butanol-to-AA ratios in the reactor which yield butanol-rich effluents are favorable for the BA/AA separation and yield the wide (8.5:1–17:1) aqueous reflux operating windows, as described. In the event that the reactor cannot be operated under the above conditions, a provision for a separate fresh butanol stream fed directly to the AA separation column can be made to ensure a wide aqueous mode operating window independent of the reactor conditions. Fresh butanol is best fed at or slightly below the main feed. Butanol should never be fed above the main, AA-containing feed. (As a light component, feeding butanol above the main feed allows it to flash overhead quickly, leaving the trays between the main-feed and butanol feed with little butanol to suppress AA volatility.)

Laboratory Confirmation of the Aqueous and Organic Modes

The existence of two steady states in the AA separation column was confirmed experimentally in a multi-day continuous laboratory run, from which Examples 1–6 and Comparative Examples 1–2 were taken. Material flow rates in Table 1 and in the simulations that generated FIG. 2 were modeled on a plant-scale; in the acrylic acid separation column Examples below, flow rates were scaled down such that 250 Kg (550 lbs)/hr on the above plant scale model were equivalent to 1 g/hr in this laboratory run. The extended run, which approximately followed the points circled in FIG. 2, started out by demonstrating continuous operation of the column in the aqueous mode for various reflux flow rates, Points 1 and 2. This portion of the run was followed by an intentional decrease of reflux water to drive the column to organic mode operation, Points 3 and 4. Subsequent changes of boil-up conditions then were imposed to restore the column to aqueous operation. In FIG. 2, points 1 and 5, 2 and 4, 6 and 8, represent pairs of matching points, i.e., points of equal reflux flow rate in the aqueous and organic modes, respectively. The aqueous mode, once achieved, was maintained by a reflux ratio of from 8.5:1 to 17:1, and yielded distilled BA having the desired level of AA, <2,000 ppm and also a separated aqueous AA stream having substantially no BA. The measured levels of AA in BA at points 1 and 2 were 950 ppm and 200 ppm AA, respectively, and of BA in AA, none (<1 ppm) was measured.

Example 1
Aqueous Mode Operation at Aqueous Reflux Ratio of 16 (Point 1 of FIG. 2)

The acrylic acid separation column 15 was a 30-tray, 1-inch diameter, Oldershaw fractional distillation column equipped with a glass condenser in line 16 and a stainless steel steam reboiler. The column was operated at an overhead pressure of 75 mm Hg. The acrylic acid separation column was fed per hour with 10.8 g (0.15 mol) of AA, 30.6 g (0.41 mol) of butanol, 82.4 g (0.64 mol) of BA, and 12.0 g (0.67 mol) of water. This mixture composition corresponded to a reactor condensate generated in a system where the reactor 1 operated at an AA-to-BuOH ratio of 1:1.35 and at a conversion of 80% on AA while receiving per hour 0.18 g of recycled BA per gram of unreacted BuOH and 0.11 g of recycled water per gram of unreacted AA. The feed tray was the 10th tray from the bottom. The overhead mixture distilled at a temperature of 43.5° C. and was condensed and separated into two phases in the receiver 18. Of the BA-rich organic phase 19, 117.3 g/h (grams per hour) were collected which contained, by weight, 70.3% BA, 26.0% butanol, 3.6% water, and 0.1% AA. Of the separated aqueous phase 20, 110.2 g/h (94.3% of the phase) was recycled to the top of the column through line 21 and 6.7 g/h (5.7%) was moved forward through line 22, yielding an aqueous reflux ratio of 16.4. The aqueous phase contained 96.6% water, 3.2% butanol, 0.2% BA, and 354 ppm AA. Of the AA-rich bottom product, stream 17, 12.0 g/h were collected containing 89.2% AA and 10.8% water. The resulting bottom temperature was 60.0° C. Ex. 1 corresponded to point 1 in FIG. 2.

Example 2
Aqueous Mode Operation at Aqueous Reflux Ratio of 11 (Pt. 2 of FIG. 2)

The apparatus, feed rate, feed composition, feed location, column pressure and general column operation were the same as those described in Ex. 1. Steam to the reboiler and aqueous condensate return rate were reduced in order to reduce the aqueous reflux flow to the column. The overhead product in line 16 obtained at a temperature of 42.6° C. was condensed and separated into two phases in receiver 18. 117.1 g/h of the BA-rich organic phase 19 were collected which contained 70.4% BA, 26.0% butanol, 3.6% water, and 218 ppm of AA. Of the separated aqueous phase 20, 77.2 g/h (91.8%) were recycled to the top of the column through line 21 and 6.9 g/h (8.2%) were moved forward through line 22, yielding an aqueous reflux ratio of 11.2. The aqueous phase contained 96.6% water, 3.2% butanol, 0.2% BA, and 81 ppm AA. 12.0 g/h of the bottom product by line 17 were collected containing 90.0% AA and 10.0% water. The resulting bottom temperature was 60.4° C. This Example corresponded to point 2 in FIG. 2.

Comparative Example 1
Organic-mode Operation (Pt. 3 of FIG. 2)

The apparatus, feed rate, feed composition, feed location, and column pressure and general column operation were the same as those described in Ex. 1 and the column was initially operated in a fashion identical to Ex. 2. Steam to the reboiler and aqueous condensate return rate were then reduced in order to further reduce the aqueous reflux flow to the column. The overhead product through 16 obtained at a temperature of 50.1° C. was condensed and separated into two phases in receiver 18. 118.5 g/h of the BA-rich organic phase 19 were collected which contained 62.6% BA, 25.6% butanol, 6.1% AA, and 5.7% water. Of the separated aqueous phase 20, 36.0 g/h (86.2%) were recycled to the top of the column through line 21 and 5.8 g/h (13.8%) were moved forward through line 22, yielding an aqueous reflux ratio of 6.3. The aqueous phase contained 94.4% water, 3.1% butanol, 2.2% AA, and 0.3% BA. 11.8 g/h of the bottom product via 17 were collected containing 70.7% BA, 29.1% AA and 0.2% butanol. The resulting bottom temperature was 88.3° C. This Example corresponded to point 3 in FIG. 2 and demonstrated that operating the column at a reflux ratio below the reflux ratio range of the present invention leads to undesired organic-mode operation. The results included high levels of AA in the BA-rich organic phase 19, high levels of BA in the bottom stream 17 and high column temperatures relative to the aqueous mode conditions of Examples 1–2.

Comparative Example 2
Confirmation of Two Steady States

The apparatus, feed rate, feed composition, feed location, and column pressure were the same as those described in Ex. 1 and the column was initially operated under conditions identical to the completion of Comp. Ex. 1. Steam to the reboiler and aqueous condensate return rate were then increased in order to raise the aqueous reflux to the column to the same flow rate as in Ex. 2 (point 2 in FIG. 1). The overhead product through line 16 obtained at a temperature of 43.9° C. was condensed and separated into two phases in the receiver 18. 117.9 g/h of the BA-rich organic phase 19 were collected which contained 63.9% BA, 25.8% butanol, 5.2% water, and 5.1% AA. Of the aqueous phase 20, 77.2 g/h (92.5%) were recycled to the top of the column through line 21 and 6.2 g/h (7.5%) were moved forward through line 22, yielding an aqueous reflux ratio of 12.4. The aqueous phase contained 94.7% water, 3.1% butanol, 1.9% AA, and 0.3% BA. 11.9 g/h of the bottom product through 17 were collected containing 60.4% BA, 39.2% AA and 0.4% butanol. The resulting bottom temperature was 88.3° C. This Comparative. Ex. corresponded to point 4 in FIG. 2 and showed that even with a reflux flow rate of 77.2 g/hr, the same as in Example 2, and an aqueous reflux ratio of 12.4, the column remained in the undesired state of organic mode operation and gave high levels of AA in the organic distillate and of BA in the bottom stream, and high column temperatures, relative to results under aqueous mode conditions of Examples 1 and 2.

By demonstrating the existence of Point 4 in FIG. 2, the organic mode point analogous to aqueous mode point 2, this Comparative Example demonstrated that two steady states indeed exist in the column as predicted by the modeling described above. This Comparative Example also demonstrated that the two steady state branches form a "hysteresis loop" and that once the column is operating in the undesired organic mode, with sufficient heat input it remained in that mode of operation even after the aqueous reflux ratio rate has been increased to a level effective in aqueous mode operation.

Example 3
Restoration of Aqueous Mode Operation from Organic Mode Operation

The apparatus, feed rate, feed composition, feed location, and column pressure were the same as described in Ex. 1. The column was initially operated at point 3 of FIG. 2 in a run identical to Comp. Ex. 1. To the top tray of the column was then added a stream of water at a rate of 41.2 g/h. Combined with the original 36.0 g/h of aqueous reflux, this additional water stream provided an effective reflux flow to the column of 77.2 g/h, the same reflux rate as in Example 2 and Comp. Ex. 2, i.e., points 2 and 4, respectively, in FIG. 2. Reboiler steam input was maintained at the same level as in Comp. Ex. 1 (point 3 of FIG. 2). Through thermocouples placed in alternate trays, a cool front, primarily of liquid water, was observed to move down the column, starting at the top tray and descending one tray at a time until it eventually reached the reboiler. Thus, with no additional steam provided to the reboiler to handle the higher load, the additional water fed to the top tray behaved as expected, in providing a cooling effect to all trays. Once the cool front reached the reboiler, indicated by a sharp temperature drop from 88.3° C. to 57.0° C., the additional fresh water stream to the top tray was discontinued and reboiler steam flow rates were increased to raise the aqueous reflux rate from 36.0 g/h to 77.2 g/h, and the column was allowed to reach steady state, now in the aqueous mode, at the higher reflux rate.

The overhead mixture through line 16 obtained at a temperature of 42.6° C. was condensed and separated into two phases in receiver 18; 117.0 g/h of the BA-rich organic phase 19 were collected which contained 70.5% BA, 26.0% butanol, 3.5% water, and 263 ppm of AA. Of the separated aqueous phase 20, 77.2 g/h (91.8%) were recycled to the top of the column through line 21 and 6.9 g/h (8.2%) were moved forward through line 22, yielding an aqueous reflux ratio of 11.2. The aqueous phase contained 96.6% water, 3.2% butanol, 0.2% BA, and 75 ppm AA. 12.1 g/h of the AA rich bottom stream 17 were collected containing 89.5 weight % AA and 10.5 weight % water. The resulting bottom temperature was 60.2° C. This outcome corresponded to point 2 in FIG. 2 and was substantially identical to that of Ex. 2. Thus, Ex. 3 demonstrated a short-cut method to return the column to the desired aqueous mode operation from a point on the organic mode branch. In the aqueous mode, the acrylic acid separation column is run with water in all trays and in the bottom stream 17 while in the undesired organic mode, water concentrates in the top several trays and bottom stream 17 is devoid of water. Although in this Example the acrylic acid separation column started in the organic mode, by the treatment shown the column was made operable in the desired aqueous mode. This result was especially important in view of the findings of Comp. Ex. 2 which had confirmed that the two steady states in this particular system for producing BA form the "hysteresis loop" as shown in FIG. 2.

Example 4
Aqueous Mode Operation at Aqueous Reflux Ratio of 9.6

Using apparatus described in Example 1, the column was operated at an overhead pressure of 75 mm Hg and was fed per hour with 5.6 g (0.08 mol) of AA, 34.8 g (0.47 mol) of butanol, 96.4 g (0.75 mol) of BA, and 13.1 g (0.73 mol) of water. This mixture composition corresponded to a reactor vaporized mixture generated in BA esterification wherein the reactor 1 operated at an AA-to-butanol ratio of 1:1.5 and conversion of 90% on AA, recycling 18% of BA per unit wt. of unreacted butanol via stream 52 and 7% of water per unit wt. of unreacted AA via stream 17. The feed tray was the 10th tray from the bottom. The overhead distillate 16 obtained at a temperature of 42.2° C. was condensed and separated into two phases in the receiver 18. 135.8 g/h of the BA-rich organic phase 19 were collected; it contained 71.0 weight % BA, 25.5 weight % butanol, 3.5 weight % water, and 550 ppm of AA. Of the aqueous phase 20, 78.9 g/h (90.6%) were recycled to the top of the column through stream 21 and 8.2 g/h (9.4%) were moved forward through stream 22, thus providing an aqueous reflux ratio of 9.6. The separated aqueous phase contained 96.7 weight % water, 3.1 weight % butanol, 0.2 weight % BA, and 209 ppm AA. 6.0 g/h of the AA-rich bottom stream by line 17 were collected containing 93.1 weight % AA and 6.9 weight % water.

Example 5
Aqueous Mode Operation at Aqueous Reflux Ratio of 11.0

The apparatus, feed rate, feed composition, feed location, and column pressure were the same as in Example 4. The overhead mixture in 16 obtained at a temperature of 41.9° C. was condensed and separated into two phases in receiver 18. 135.9 g/h of the BA-rich organic phase 19 were collected and contained 70.9 weight % BA, 25.4 weight % butanol, 3.5 weight % water, and 779 ppm of AA. Of the aqueous phase 20, 89.5 g/h (91.6%) were recycled back to the top of the column through stream 21 and 8.2 g/h (8.4%) were moved forward through stream 22, for an aqueous reflux ratio of 11.0. The aqueous phase contained 96.7 weight % water, 3.1 weight % butanol, 0.2 weight % BA, and 286 ppm AA. 6.0 g/h of the AA-rich bottom stream 17 were collected containing 92.8 weight % AA and 7.2 weight % water. This Example demonstrated an increase of AA in the BA-rich organic phase from 550 ppm to 779 ppm, under these conditions, as the amount of aqueous reflux increased relative to that of Example 4 (9.6 reflux ratio).

Example 6
Aqueous Mode Operation at Aqueous Reflux Ratio of 9.7 with a 35-tray Column A five-tray section was added to the apparatus used in Example 1, thus providing a 35-tray, 1-inch diameter, Oldershaw fractional distillation column equipped with a glass condenser and stainless steel steam reboiler. The feed rate, feed composition, feed location, and column pressure were the same as those of Example 4. The overhead mixture in 16 obtained at a temperature of 42.2° C. was condensed and separated into two phases in receiver 18. 135.8 g/h of the BA-rich organic phase 19 were collected which contained 71.0 weight % BA, 25.5 weight % butanol, 3.5 weight % water, and 193 ppm of AA. Of the separated aqueous phase 20, 78.9 g/h (90.7%) were recycled to the top of the column through stream 21 and 8.1 g/h (9.3%) were moved forward through stream 22, for an aqueous reflux ratio of 9.7. The aqueous phase contained 96.7 weight % water, 3.1 weight % butanol, 0.2 weight % BA, and 72 ppm AA. 6.1 g/h of the AA-rich bottom stream 17 were collected containing 92.5 weight % AA and 7.5 weight % water. The resulting bottom temperature was 62.3° C. This Example demonstrated that adding 5 trays to the rectifying section of the AA separation column further reduced AA in the BA-rich organic phase from 550 ppm in Ex. 4 to 193 ppm.

Comparative Example 3

Cracking Reactor Processing Without Use of an HRU

This comparative example was performed in the above described 500 ml cracking reactor, using feed streams described and without use of a HRU. Thus, 73.46 g/hr of a feed containing the composition listed in table 2 was fed to a CFSTR maintained at 130° C., 35 mm Hg pressure, 60 min. residence time, and a catalyst concentration of 8.07 wt % $H_2SO_4$. A total of 55.24 g/hr of a single phase distillate was recovered with the composition listed in table 3. A bleed stream of 18.22 g/hr was bled from the cracking reactor and discarded as waste oil. The AA and BuOH recovered values are summarized in tables 10 and 11, which shows that, after recovery of free values, only 15.0% of the AA values in heavies and 11.6% of BuOH values in heavies were recovered.

TABLE 2

Feed Stream Composition for Comparative Example 3

| Feed Stream Components | g/hr in Feed | mmol/hr in Feed Stream | mmol/hr Values | |
|---|---|---|---|---|
| | | | mm Bu | mm AA |
| BuOH | 0.70 | 9 | 9 | 0 |
| BA | 31.66 | 247 | 247 | 247 |
| AA | 15.65 | 217 | 0 | 217 |
| BBBP | 1.47 | 7 | 14 | 7 |
| BBHP | 0.41 | 3 | 3 | 3 |
| BAOPA | 3.89 | 19 | 19 | 38 |
| AOPA | 3.60 | 25 | 0 | 50 |
| Butyl Maleate | 1.47 | 9 | 9 | 0 |
| $BuOSO_2OH$ | 2.31* | 15 | 15 | 0 |
| "Heavies Mixture" | 10.10 | 69 | 69 | 69 |
| Inhibitor | 2.20 | NA | | |
| Totals | 73.46 | | 385 | 631 |

*1.47 g/hr calculated as $H_2SO_4$

TABLE 3

Distilled Overhead Stream Composition of Comparative Example 3

| Feed Stream Components | g/hr | mmol/hr | mmol/hr Values | |
|---|---|---|---|---|
| | | | mm Bu | mm AA |
| BuOH | 0.884 | 12 | 12 | |
| BA | 33.199 | 259 | 259 | 259 |
| AA | 16.572 | 230 | 0 | 230 |
| BBBP | 0.718 | 4 | 8 | 4 |
| Water | 0.829 | 46 | | |
| Dibutyl Ether | 0.017 | 0.13 | 0.13 | 0 |
| High Boilers | 3.022 | NA | | |
| Totals | 55.24 | | 271 | 489 |

Example 7
HRU Evaluation Under Effective Conditions

A total of 73.46 g of organic feed containing the composition listed in Table 4 was fed to the HRU maintained at a temperature of 108° C., 760 mm Hg, 144 min. residence time, 16 wt % reactor water, and a catalyst concentration of 2.7 wt % $H_2SO_4$. In addition, 48.0 g/hr of esterification reactor first aqueous distillate (comprising 93.0% $H_2O$, 6.0% AA, and 1.0% BUOH) also was fed to the HRU to compensate for water distilled and removed with the organic distillate and reactor bleed and to simulate recycle of the aqueous distillate to the HRU. A total of 39.35 g/hr of organic distillate and 38.27 g/hr of aqueous distillate were collected and analyzed. The results of the analysis are summarized in Table 5. The organic phase was separated for return to an esterification reactor, when used. A bleed stream of 43.24 g/hr was bled from the HRU and constituted the total feed to the bleed stripper CFSTR.

TABLE 4
Feed Stream Composition for HRU Feed, Example 7

| Feed Stream Components | g/hr in Feed | mmol/hr in Stream | mmol/hr Values mm Bu | mm AA |
|---|---|---|---|---|
| BuOH | 0.85 | 11 | 11 | 0 |
| BA | 32.627 | 255 | 255 | 255 |
| AA | 15.471 | 215 | 0 | 215 |
| BBBP | 0.951 | 5 | 10 | 5 |
| BBHP | 0.410 | 3 | 3 | 3 |
| BAOPA | 7.320 | 37 | 37 | 74 |
| AOPA | 1.57 | 11 | 0 | 22 |
| Butyl Maleate | 0.712 | 4 | 4 | 0 |
| BuOSO$_2$OH* | 2.309 | 15 | 15 | |
| Heavies Mixture | 9.034 | 62 | 62 | 62 |
| Inhibitor | 2.20 | NA | | |
| Totals | 73.46 | | 397 | 636 |

*1.47 g calculated as $H_2SO_4$

TABLE 5
Compositions of Streams from HRU Evaluation of Example 7

| Component | Org. Phase g/hr | Organic mmol/hr Values | mmol/hr Values Bu | mmol/hr Values AA | Aqueous Phase g/hr |
|---|---|---|---|---|---|
| BuOH | 3.959 | 54 | 54 | 0 | 1.102 |
| BA | 28.159 | 220 | 220 | 220 | — |
| AA | 5.245 | 73 | 0 | 73 | 2.465 |
| BBBP | 0.014 | 0.07 | .14 | .07 | — |
| Water | 1.624 | 90 | — | — | 34.703 |
| DBF | 0.028 | 0.22 | .44 | .44 | — |
| High Boilers | 0.321 | — | — | — | — |
| Totals | 39.350 | 347 | 274 | 293 | 38.270 |

Example 8
Cracking Reactor Evaluation Under Effective Conditions

The total of 43.24 g/hr of the HRU bleed stream from Example 7 was fed to the cracking reactor CSTR described above and held at a temperature of 130° C. at 100 mm Hg pressure, and a residence time of 120 min. A total of 33.63 g of distillate, the cracking reactor overhead stream, was obtained for return to an esterification reactor. A total of 9.61 g/hr of cracking reactor residue stream was collected and discarded as waste oil. The total AA and BuOH recoveries for the combination of both units (HRU and cracking reactor) is summarized in Tables 10 and 11. The results show that, after recovery of free values, 68.7% of the AA values in heavies and 59.5% of the BuOH values in heavies were recovered.

TABLE 6
Composition of the Cracking Reactor Overhead Stream of Example 8

| Cracking Reactor Overhead Stream Components | g/hr | mmol/hr | mmol/hr Values mm Bu | mmol/hr Values mm AA |
|---|---|---|---|---|
| BuOH | 0.789 | 11 | 11 | 0 |
| BA | 7.572 | 59 | 59 | 59 |
| AA | 16.716 | 232 | 0 | 232 |
| Water | 7.750 | 431 | | |
| High Boilers | 0.803 | — | — | — |
| Totals | 33.630 | | 70 | 291 |

Example 9
HRU Evaluation under More Severe Conditions and with a Cracking Reactor in Tandem This example under more severe HRU operating conditions (higher acid concentration) than in Ex's. 7 and 8 afforded higher recovery of AA and BuOH values. Thus, 73.46 g/hr of a feed stream with the composition listed in Table 7 was fed to the HRU maintained at 114° C., 760 mm Hg, 5.1 wt % $H_2SO_4$ (7.5 wt % by mass balance (MB)), 144 min. residence time, and a water concentration of 15.5 wt %. In addition, 46.48 g of aqueous feed comprising 93% water, 6% AA, and 1% butanol was fed to the HRU to simulate recycle of the aqueous distillate plus makeup of water lost to the organic distillate and bottoms bleed. A total of 41.96 g/hr of HRU organic distillate (composition in Table 8), 38.80 g/hr of HRU aqueous distillate, and 28.22 g/hr of cracking reactor overhead stream (composition in Table 9) were recovered and analyzed. The cracking reactor overhead stream was obtained by feeding the HRU bleed stream (39.18 g/hr) to the cracking reactor maintained at the following conditions: 130° C., 100 mm Hg, 120 min. residence time, 26.8% $H_2SO_4$ (by MB). The total AA and BuOH recoveries for this tandem combination are listed in Tables 10 and 11 and show that, after recovery of free values, 81.7% of the AA values and 65.2% of the BuOH values in heavies were recovered.

TABLE 7
Feed Stream Composition for Example 9

| Component | g/hr Feed | mmol/hr Feed | mmol/hr Values Bu | mmol/hr Values AA |
|---|---|---|---|---|
| BuOH | 0.528 | 7 | 7 | 0 |
| BA | 32.480 | 254 | 254 | 254 |
| AA | 15.324 | 213 | 0 | 213 |
| BBBP | 0.804 | 4 | 8 | 4 |
| BBHP | 0.263 | 2 | 2 | 2 |
| BAOPA | 7.173 | 36 | 36 | 72 |
| AOPA | 1.423 | 10 | 0 | 20 |
| Butyl Maleate | 0.565 | 4 | 4 | 0 |
| BuHSO$_4$ | 4.618* | 30.0 | 30 | 0 |
| Heavies Mixture | 8.078 | 55 | 55 | 55 |
| Inhibitor | 2.20 | NA | | |
| Totals | 73.46 | | 396 | 620 |

*2.94 calculated as $H_2SO_4$

TABLE 8

Compositions of Streams from HRU Evaluation of Example 9

| Component | Org. phase g/hr | Org. wt % | Org mmol/hr | mmol/hr Values Bu | AA |
|---|---|---|---|---|---|
| BuOH | 4.126 | 9.832 | 56 | 56 | 0 |
| BA | 30.438 | 72.54 | 238 | 238 | 238 |
| AA | 6.331 | 15.089 | 88 | 0 | 88 |
| BBBP | 0.047 | 0.112 | 0.23 | | |
| Water | 0.985 | 2.347 | 55 | | |
| DBE | 0.034 | 0.081 | 0.26 | | |
| High Boilers | — | — | — | | |
| Totals | 41.96 | | | 294 | 326 |

TABLE 9

Composition of the Cracking Reactor Overhead Stream of Example 9

| Component | g/hr | wt % | mmol/hr | mmol/hr Values Bu | AA |
|---|---|---|---|---|---|
| BuOH | 0.391 | 1.387 | 5.28 | 5 | 0 |
| BA | 6.364 | 22.552 | 50 | 50 | 50 |
| AA | 15.566 | 55.161 | 216 | | 216 |
| Water | 5.765 | 20.428 | 320 | | |
| High Boilers | 0.132 | 0.466 | — | | |
| DBB | 0.002 | | | | |
| Totals | 28.226 | | | 55 | 266 |

Example 10
Continuous Process for Producing Butyl Acrylate

The esterification reactor 1 was a 2 L round bottom, Pyrex, flask equipped with a two plate (5.0 cm diameter) Oldershaw distillation column (serving as an acid catalyst entrainment separator), a condenser, thermocouple, feed ports attached to appropriate fluid metering pumps, and lines leading to a hydrolytic reactor unit (HRU, 5) and cracking reactor 10, described more fully below. Reactor working capacity was 750 ml of reaction mixture containing 2.50 wt % of sulfuric acid catalyst. The reaction temperature was 89° C. and the pressure was 127 mm Hg. Reactor 1 was fed with 182.90 g/hr of fresh crude AA (assay: 96% AA by weight, 2435 mmol/hr), 182.48 g/hr of fresh n-butanol (BuOH, 2466 mmol/hr), and 1.71 g/hr of fresh $H_2SO_4$ (95.5 wt % acid). The reactor was fed with a total of 655.3 g/hr of material composed of 223.85 g/hr AA (3105 mmol/ hr), 316.90 g/hr BuOH (4282 mmol/ hr), an HRU condensed and separated overhead organic stream, a cracking reactor overhead condensate, an AA separation column bottom stream, and a BA/BuOH/$H_2O$ mixture representing streams from recovery and recycle of the following streams: (a) unreacted BuOH in a downstream BuOH/BA azeotropic distillation column; (b) a BuOH/BA recovery stream from stripping of waste aqueous streams before sending the stream to waste treatment; and (c) a portion of final product distillation column bottoms. (These streams comprise the typical feed and supplemental (e.g. recycle) streams used in a representative plant continuous process). The total BA thus fed to the esterification reactor from these sources was 88.07 g/hr (688 mmol/ hr), of which 50.85 g/hr represents recycle from downstream separation columns. AA and BuOH were accordingly used in a mole ratio of 1:1.38.

The reactor was maintained at a residence time of approximately 60 minutes whereby 749.8 g/hr of total material was distilled off as the reactor overhead distillate through the Oldershaw column, condensed, and separated in two phases. A portion of the organic phase (160 g/hr) was returned to the head of the distillation column as reflux. The remaining 563.8 g/hr of organic distillate containing 38.56 g/hr of AA, 124.59 g/hr of BuOH, and 371.24 g/hr of BA was fed to the acrylic acid separation column, 15. The reactor's aqueous condensed vaporized mixture was separated (26.0 g/hr containing 2.12 g/hr of BuOH and 0.619 g/hr of AA) and split in the following fashion: 22.4 g/hr to the AA separation column via line 53 and 3.6 g/hr to the HRU, via 42.

The HRU 5 and cracking reactor 10 are identical to those described in Examples 7, 8, and 9. Accordingly, 65.5 g/hr of esterification reactor bleed stream containing 4.33 g/hr of BuOH, 6.19 g/hr of AA, 34.23 g/hr of BA, and other related high boilers and inhibitors were fed to HRU 5 via line 3 and maintained at 122° C., 760 mm Hg pressure, 317 min residence time, 6.26 wt % $H_2O$, and an acid catalyst concentration of 7.58 wt % $H_2SO_4$. Additionally 3.6 g/hr of reactor aqueous condensed distillate was fed to the HRU. From the HRU, a total of 80.5 g/hr of material was distilled as an overhead stream, condensed, and separated. The entire separated aqueous phase (38.3 g/hr, containing 2.47 g/hr of BuOH and 1.01 g/hr of AA) was returned to the HRU as reflux via 7. The separated organic phase (42.1 g/hr containing 7.07 g/hr BuOH, 3.19 g/hr AA, and 29.72 g/hr BA) was returned to the esterification reactor as a recovered recycle stream via 8. A bleed stream of 27.0 g/hr was removed from the HRU via 9 and fed to cracking reactor 10 maintained at 120° C., 35 mm Hg pressure, 815 min residence time, and 20.5 wt % $H_2SO_4$. A total of 17 g/hr (containing 0.397 g/hr BuOH, 8.44 g/hr AA, and 4.78 g/hr BA) of material was distilled off and condensed in 31. This combined condensate was returned via 12 to the esterification reactor as recycle. The bleed stream from the cracking reactor was discarded as waste oil via 13.

The acrylic acid separation column 15 consisted of a 35 plate, 5.0 cm diameter, Oldershaw distillation column equipped with a steam jacketed, stainless steel, reboiler and water cooled condenser system. Accordingly, 563.8 g/hr of esterification reactor organic layer condensed distillate and 22.4 g/hr of ester reactor aqueous layer condensed distillate (composition described above) were fed to 15 operated at a head pressure of 260 mm Hg, a base temperature of 82° C., and an aqueous reflux ratio of 9.61. A total of 907.3 g/hr of overhead mixture was obtained by distillation through the column, condensed, and separated, in 18. A total of 400.7 g/hr of separated aqueous phase was collected of which 363.4 g/hr was returned to the head of the column as reflux vial line 21. The BA-rich organic phase (506.60 g/hr) containing the BA product was substantially free of AA (1450 ppm). An AA-rich bottom stream of 42.3 g/hr was removed from the column (35.35 g/hr AA) and recycled via 17 to the esterification reactor. Recovery data are included in Tables 10 and 11.

With the entire BA process operated in this fashion, a quantitative yield of BA on BuOH was realized and a 102.7% yield of BA on AA was realized (of a 104.8% theoretical yield, based on the AA and AOPA content of the fresh crude AA charged).

Example 11
Continuous Process for Producing BA, Including Recycle of Additional Streams The esterification reactor and related process equipment utilized in this Example is identical to that described in Example 10. Reactor working capacity was 1000 ml of reaction mixture containing 2.25 wt % of sulfuric acid catalyst. All working units were fed as herafter described. Reactor 1 was fed with 183.90 g/hr of fresh crude AA (assay: 96% AA by weight, 2449 mmol/hr), 207.03 g/hr of fresh n-butanol (BuOH, 2798 mmol/hr), and 2.05 g/hr of fresh $H_2SO_4$ (95.5 wt % acid). The HRU was fed via additional streams of 30.58 g/hr (424 mmol/hr) of AA and 4.11 g/hr (55.5 mmol/hr) of BuOH bringing the total fresh AA feed to the system to 207.12 g/hr (2873 mmol/hr) and the total fresh BuOH feed to 211.14 g/hr (2853 mmol/hr). Reactor 1 thus was fed with a total of 866.9 g/hr of material composed of: 260.10 g/hr AA (3607 mmol/hr), 406.6 g/hr BuOH (5495 mmol/hr), an HRU overhead condensed organic layer, a cracking reactor overhead stream, an AA separation column bottom stream, and a BA/ BuOH/ $H_2O$ mixture representing streams from recovery and recycle of the following streams: (a) unreacted BuOH in a downstream BuOH/BA azeotropic distillation column; (b) a BuOH/BA recovery stream from stripping of waste aqueous streams before sending the stream to waste treatment; and (c) a portion of final product distillation column bottoms. (These streams comprise the typical feed and recycled streams used in a fully integrated plant continuous process). The total BA fed to the esterification reactor from these sources was 144.6 g/hr, of which 84.14 g/hr represented recycled BA from downstream separation columns and supplemental waste streams. AA and BuOH were accordingly used in reactor 1 in a mole ratio of 1:1.52.

The reactor was maintained at a residence time of approximately 60 minutes whereby 995.9 g/hr of total material was distilled as the reactor overhead distillate through the Oldershaw distillation column, condensed, and separated in two phases. A portion of the organic phase (216.1 g/hr) was returned to the head of the distillation column as reflux. The remaining 719.8 g/hr of organic distillate containing 45.20 g/hr of AA, 183.10 g/hr of BuOH, and 451.0 g/hr of BA was fed to the acrylic acid separation column, 15, which is described below. The reactor aqueous distillate (60.10 g/hr containing 4.78 g/hr of BuOH and 1.06 g/hr of AA) was split in the following fashion: 36.5 g hr to the AA separation column and 23.6 g/hr to the HRU.

The HRU 5 and cracking reactor 10 are identical to those described in Examples 7, 8, and 9. Accordingly 87.1 g/hr of esterification reactor bleed stream via line 3 and 128.7 g/hr of additional streams containing 11.3 g/hr of BuOH, 38.3 g/hr of AA, 37.1 g/hr of BA, and other related high boilers and inhibitors via line 4 were fed to the HRU maintained at 122° C., 760 mm Hg pressure, 150 min residence time, 12.8 wt % $H_2O$, and a catalyst concentration of 9.3 wt % $H_2SO_4$.

Additionally 23.60 g/hr of reactor aqueous distillate was fed to the HRU. From the HRU, a total of 198.7 g/hr of material was distilled, condensed, and separated. The entire aqueous distillate (114.6 g/hr, containing 4.35 g/hr of BuOH and 6.25 g/hr of AA) was returned to the HRU as reflux via line 7. The organic distillate (84.1 g/hr, containing 12.2 g/hr BuOH, 9.94 g/hr AA, and 56.3 g/hr BA) was returned to the esterification reactor as recycle via line 8. An HRU bleed stream of 155.2 g/hr was removed from the HRU bottom and fed to cracking reactor 10 maintained at 120° C., 35 mm Hg pressure, 180 min residence time, and 24.0 wt % $H_2SO_4$. A total of 70.6 g hr (containing 2.00 g/hr BuOH, 34.3 g/hr AA, and 9.29 g/hr BA) of cracking reactor overhead stream was distilled and condensed. This condensate was recovered and returned to the main esterification reactor as a recycled stream and the cracking reactor bottom bleed stream was discarded as waste oil.

The acrylic acid separation column 15 consisted of a 35 plate, 5.0 cm diameter, Oldershaw distillation column equipped with a steam jacketed, stainless steel, reboiler and water cooled condenser system. Accordingly, 719.8 g/hr of esterification reactor organic distillate condensate and 36.5 g/hr of reactor aqueous distillate condensate (compositions as described above) were fed to the acrylic acid separation column operated at a head pressure of 260 mm Hg, a base temperature of 82° C., and an aqueous reflux ratio of 12.5. A total of 1193.8 g/hr of overhead mixture was obtained by distillation through the AA separation column, condensed, and separated. A total of 526.4 g/hr of separated aqueous phase was collected of which 487.9 g/hr was returned to the head of the AA separation column as reflux via line 21, the balance of the aqueous phase moved forward with the remainder of the condensate. The BA-rich organic phase (667.4 g/hr) containing the BA product was also moved forward for further isolation; it was substantially free of AA, containing 1500 ppm AA. An AA-rich bottom stream of 50.4 g/hr was removed from the AA separation column (43.56 g/hr AA) and recycled via 17 to the esterification reactor. Recovery data are included in Tables 10 and 11.

With the entire process for producing BA operated in the process described Example, a BA yield based on BuOH was 100.5%; on AA, a BA yield of 99.8% was realized.

TABLE 10

Summary of AA Values Fed and Recovered

| Example Number | Free AA Values Fed (mmol) | AA Values In Heavies (mmol) | Total AA Values Fed (mmol) | AA Values Recovered From Heavies (mmol) | Total AA Values Recovered (mmol) | % AA Recovery From Heavies | Total % AA Recovery |
|---|---|---|---|---|---|---|---|
| Comp. Ex. 3 | 464 | 167 | 631 | 25 | 489 | 15.0% | 77.5% |
| Ex.'s 7–8 | 470 | 166 | 636 | 114 | 584 | 68.7% | 91.8% |
| Ex. 9 | 467 | 153 | 620 | 125 | 592 | 81.7% | 95.5% |
| 10 | 354 | 130 | 484 | 430 | 77 | 59.2% | 89.1% |
| 11 | 822 | 764 | 1586 | 1127 | 305 | 39.9% | 71.1% |

TABLE 11

Summary of BuOH Values Fed and Recovered

| Example Number | Free BuOH Values Fed (mmol) | BuOH Values In Heavies (mmol) | Total BuOH Values Fed (mmol) | BuOH Values Recovered From Heavies (mmol) | Total BuOH Values Recovered (mmol) | % BuOH Recovery From Heavies | Total % BuOH Recovery |
|---|---|---|---|---|---|---|---|
| Comp. Ex. 3 | 256 | 129 | 385 | 15 | 271 | 11.6% | 70.4% |
| Exs. 7–8 | 266 | 131 | 397 | 78 | 344 | 59.5% | 86.6% |
| Ex. 9 | 261 | 135 | 396 | 88 | 349 | 65.2% | 88.1% |
| 10 | 330 | 124 | 454 | 370 | 40 | 32.3% | 81.5% |
| 11 | 443 | 471 | 914 | 705 | 262 | 55.6% | 77.1% |

We claim:

1. A method of recovering values selected from at least one of acrylic acid, $C_1$–$C_4$ alkyl acrylates and $C_1$–$C_4$ alkanols from heavy ends produced during production of a $C_1$–$C_4$ alkyl acrylate, comprising the steps of:

(A) feeding a stream comprising the heavy ends, water, residual acid catalyst, and optionally a strong acid selected from a mineral acid or sulfonic acid, to a hydrolysis reactor;

(B) distilling an overhead stream containing the values and water from the hydrolysis reactor while maintaining a hydrolysis reactor liquid concentration of from 5 to 40 weight % water and at least 1 weight % acid, the acid comprising the residual acid catalyst and optionally the strong acid;

(C) separating from the distilled overhead stream an organic phase comprising the values and an aqueous phase comprising primarily water, and acrylic acid and the $C_1$–$C_4$ alkanol;

(D) recycling the separated aqueous phase to the hydrolysis reactor;

(E) feeding up to 100% of a bleed stream from the hydrolysis reactor to a cracking reactor;

(F) distilling from the cracking reactor an overhead stream comprising values selected from at least one of acrylic acid, the $C_1$–$C_4$ alkyl acrylate, the $C_1$–$C_4$ alkanol, and water while maintaining a cracking reactor liquid concentration of at least 7.5 weight % acid; and (G) recovering from the cracking reactor overhead stream at least one of acrylic acid, $C_1$–$C_4$ alkyl acrylate, $C_1$–$C_4$ alkanol and water.

2. The method of claim 1 wherein, the hydrolysis reactor is maintained at 90° to 140° C., 50 to 1000 mm Hg pressure, and the stream has a residence time of 0.5 to 20 hours in the hydrolysis reactor.

3. The method of claim 1 wherein, the cracking reactor is maintained at 90° to 140° C. and a pressure of from 20 to 200 mm Hg, and the bleed stream has a residence time of 0.5 to 20 hours in the cracking reactor.

4. A method of recovering values selected from at least one of acrylic acid, n-butyl acrylate and n-butanol from heavy ends produced during production of n-butyl acrylate, comprising the steps of:

(A) feeding a stream comprising the heavy ends, water, residual acid catalyst, and optionally a strong acid selected from a mineral acid or sulfonic acid, to a hydrolysis reactor;

(B) distilling an overhead stream containing the values and water from the hydrolysis reactor while maintaining a hydrolysis reactor liquid concentration of from 5 to 40 weight % water and at least 1 weight % acid, the acid comprising the residual acid catalyst and optionally the strong acid;

(C) separating from the distilled overhead stream an organic phase comprising the values and an aqueous phase comprising primarily water, and acrylic acid and the n-butanol;

(D) recycling the separated aqueous phase to the hydrolysis reactor;

(E) feeding up to 100% of a bleed stream from the hydrolysis reactor to a cracking reactor;

(F) distilling from the cracking reactor an overhead stream comprising values selected from at least one of acrylic acid, n-butyl acrylate, n-butanol, and water while maintaining a cracking reactor liquid concentration of at least 7.5 weight % acid; and (G) recovering from the cracking reactor overhead stream at least one of acrylic acid, n-butyl acrylate, n-butanol and water.

5. The method of claim 4 wherein, the hydrolysis reactor is maintained at 90° to 140° C., 50 to 1000 mm Hg pressure, and the stream has a residence time of 0.5 to 20 hours in the hydrolysis reactor.

6. The method of claim 4 wherein, the cracking reactor is maintained at 90° to 140° C. and a pressure of from 20 to 200 mm Hg, and the bleed stream has a residence time of 0.5 to 20 hours in the cracking reactor.

* * * * *